(12) United States Patent
Dong et al.

(10) Patent No.: US 9,120,732 B2
(45) Date of Patent: Sep. 1, 2015

(54) CATALYTIC ANTI-MARKOVNIKOV OXIDATION AND HYDRATION OF OLEFINS

(75) Inventors: Guangbin Dong, Pasadena, CA (US); Robert H. Grubbs, South Pasadena, CA (US); Peili Teo, Pasadena, CA (US); Zach K. Wickens, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 663 days.

(21) Appl. No.: 13/340,448

(22) Filed: Dec. 29, 2011

(65) Prior Publication Data

US 2012/0172634 A1      Jul. 5, 2012

Related U.S. Application Data

(60) Provisional application No. 61/429,061, filed on Dec. 31, 2010, provisional application No. 61/490,497, filed on May 26, 2011, provisional application No. 61/538,726, filed on Sep. 23, 2011, provisional application No. 61/564,738, filed on Nov. 29, 2011.

(51) Int. Cl.
| | | |
|---|---|---|
| *C07C 29/14* | (2006.01) | |
| *C07C 45/30* | (2006.01) | |
| *C07C 29/03* | (2006.01) | |
| *C07C 201/12* | (2006.01) | |

(52) U.S. Cl.
CPC ............... *C07C 45/30* (2013.01); *C07C 29/03* (2013.01); *C07C 29/14* (2013.01); *C07C 201/12* (2013.01)

(58) Field of Classification Search
CPC .............................. C07C 29/141; C07C 45/34
USPC ................................................. 568/401, 881
See application file for complete search history.

(56) References Cited

U.S. PATENT DOCUMENTS

| | | | |
|---|---|---|---|
| 4,661,642 | A | 4/1987 | Feringa |
| 5,506,363 | A | 4/1996 | Grate et al. |
| 2014/0194604 | A1 | 7/2014 | Morandi |
| 2014/0316149 | A1 | 10/2014 | Wickens et al. |

FOREIGN PATENT DOCUMENTS

EP           0395729 B1      9/1995

OTHER PUBLICATIONS

Muzart, "Aldehydes from Pd-catalysed oxidation of terminal olefins", Tetrahedron, Aug. 6, 2007, vol. 63, Issue 32, pp. 7505-7521.
Beller et al., "Catalytic Markovnikov and anti-Markovnikov Functionalization of Alkenes and Alkynes: Recent Developments and Trends", Agnew. Chem. Int. Ed., 2004, vol. 43, 3368-3398.
Dong et al., "Primary Alcohols from Terminal Olefins: Formal Anti-Markovnikov Hydration via Triple Relay Catalysis", Science, Sep. 16, 2011, vol. 333, 1609-1612.
Steilmann et al., "Formation of 2-phenylethanol from styrene in the presence of zeolites and UV irradiation", Chem. Commun., Mar. 1999, 697-698.
Anderson et al., "Experimental and Computational Study of a Direct OrCoupled Wacker Oxidation: Water Dependence in the Absence of Cu Salts", J. Am. Chem. Soc., 2010, 132(34), 11872-11874.
Andrews et al., "The Transition-Metal Nitro-Nitrosyl Redox Couple: Catalytic Oxidation of Olefins to Ketones", J. Am. Chem. Soc., 1981, 103(10), 2894-2896.
Backvall et al., "Stereo- and Regioselective Palladium-Catalyzed 1,4-Diacetoxylation of 1,3-Dienes", J. Org. Chem., Nov. 1984, 49, 4619-4631.
Backvall et al., "Biomimetic Adrobic 1,4-Oxidation of 1,3-Dienes Catalyzed by Cobalt Tetraphenylporphyrin-Hydroquinone-Palladium(II). An Example of Triple Catalysis", J. Am. Chem. Soc., Jul. 1987, 109(15), 4750-4752.
Backvall et al., "Multi-Step Catalysis for the Oxidation of Olefins to Ketones by Molecular Oxygen in Chloride Free Media", Tetrahedron Letters, 1988, 29(23), 2885-2888.
Backvall et al., "Multistep Electron Transfer in Palladium-Catalyzed Aerobic Oxidations via a Metal Macrocycle-Quinone System", J. Am. Chem. Soc., Jun. 1990, 112, 5160-5166.
Beller, "A Personal View on Homogeneous Catalysis and its Perspectives for the Use of Renewables", Eur. J. Lipid Sci. Technol., 2008, 110(9), 789-796, Publication Online: Aug. 21, 2008.
Bronner et al., "Formal Anti-Markovnikov Hydroamination of Terminal Olefins", Chemical Science, 2013, 5, 101-106, Published Online: Sep. 19, 2013.
Campbell et al., "Overcoming the 'Oxidant Problem': Strategies to Use O2 as the Oxidant in Organometallic C-H Oxidation Reactions Catalyzed by Pd (and Cu)", Ace. Chem. Res., 2012, 45(6), 851-863, Publication Online: Jan. 23, 2012.
Carma et al., "Chemical Routes for the Transformation of Biomass into Chemicals", Chem. Rev., 2007, 107(6), 2411-2502.
Caterina et al., "The Capsaicin Receptor: A Heat-Activated ion Channel in the Pain Pathway", Nature, Oct. 23, 1997, 389, 816-824.
Chen et al., "Discovery and Characterization Of A Potent And Selective Antagonist Of Melanin-Concentrating Hormone Receptor 2", Biorg. Med. Chem Lett., 2012, 22, 363-366.
Chen et al, "Serial Ligand Catalysis: A Highly Selective Allylic C-H Oxidation", J. Am. Chem. Soc., 2005, 127, 6970-6971.
Chowdhury et al., "An Iron Catalyzed Regioselective Oxidation Of Terminal Alkenes to Aldehydes", Chem. Commun., 2012, 48, 5497-5499, Published Online: Apr. 17, 2012..
Clyne et al., "The Synthesis of 14-Membered Macrocyclic Ethers", Tetrahedron, Nov. 26, 1999, 55(48), 13659-13682.
Conley et al., "Discovery, Applications, And Catalytic Mechanisms of Shvo's Catalyst", Chem. Rev., Jan. 2010, 110(4), 2294-2312.
Cornell et al., "Discovery of a Practical Direct OrCoupled Wacker Oxidation with Pd[(-)- sparteine]CI", Org. Lett., 2006, 8(18), 4117-4120.

(Continued)

Primary Examiner — Sudhakar Katakam
(74) Attorney, Agent, or Firm — Baker & Hostetler LLP

(57) ABSTRACT

The disclosure provides a dual-catalysis system for direct conversion of olefins to alcohols. The cooperative catalytic system contains one oxidizing catalyst and one transfer-hydrogenation catalyst. A wide variety of olefins, including aromatic and aliphatic olefins, can be used as the reactant. The transformation proceeds with anti-Markovnikov selectivity, and in some aspects provides primary alcohols as major products. The disclosure further provides a system for oxidation of olefins with anti-Markovnikov selectivity.

37 Claims, 1 Drawing Sheet

(56) References Cited

OTHER PUBLICATIONS

Eilbracht et al., "Tandem Reaction Sequences Under Hydroformyla

Decharin et al., "Benzoquinone-Promoted Reaction of $O_2$ with a $Pd^{II}$-Hydridge", J. Am. Chem. Soc., 2011, 133(15), 5732-5735.

Dong et al, "Palladium-Catalyzed Selective Anti-Markovnikov Oxidation of Allylic Esters", Angw. Chem., May 2013, 125(21), 5671-5675.

Dounay et al., "Total Synthesis of the Styrchnos Alkaloid (+)-Minfiensine: Tandem Enantioselective Intramolecular Heck-Iminium ion Cyclization", J. Am. Chem. Soc., 2008, 130(15), 5368-5377, Publication Online: Feb. 28, 2008. tion Conditions: New Synthetic Applications of Transition Metal Catalysis", Chem. Rev., Oct. 1999, 99(11), 3329-3365.

Feringa, "Catalytic Oxidation of Alk-1-enes to Aldehydes", J. Chem. Soc., 1986, 909-910.

Fischetti et al., "The Mechanism of Reactions of Organopalladium Salts with Vinylcyclopropanes", J. Organomet. Chem., Sep. 1, 1985, 293(3), 391-405.

Friestad et al., "Aldehyde-Selective Wacker Oxidation in a Thiyi-Mediated Vinyl Group Transfer Route to Daunosamine", Org. Lett., 2007, 9(5), 777-780.

Fujiwara et al., "Direct C-H Functionalization of Quinones with Boronic Acids", J. Am. Chem. Soc., 2011, 133(10), 3292-3295, Publication Online: Feb. 22, 2011.

Ghosh et al., "Cu(II)-Catalyzed Olefin Migration and Prins Cyclization: Highly Diastereoselective Synthesis of Substitute Tetrahydropyrans", Org. Lett., 2011, 13(16), 4328-4331, Publication Online: Jul. 28, 2011.

Gligorich et al., "Recent Advancements and Challenges of Palladium11-catalyzed Oxidation Reactions with Molecular Oxygen as the Sole Oxidant", Chem. Commun., 2009, 26, 3854-3867.

Gooch, "Moving Past Markovnikov's Rule", J. Chem. Educ., 2001, 78(10), 1358, Publication Online: Oct. 1, 2001.

Gorczynski et al., "Activation of Peroxisome Proliferator-Activated Receptor y (PPARy) by Nitroalkene Fatty Acids: Importance of Nitration Position and Degree of Unsaturation", J. Med. Chem., 2009, 52(15), 4631-4639, Publication Online: Jul. 17, 2009.

Grennberg et al., "Acid-Induced Transferomation of Palladium(O)-Benzoquinone Complexes to Palladium(II) and Hydroquinone", Organometallics, 1993, 12(5), 1790-1793.

Grubbs, Handbook of Metathesis, Wiley-VCH 2003, vol. 1, 16 pages.

Haggin, "Chemists Seek Greater Recognition for Catalysis", Chem. Eng. News, 1993,71, 23-27.

Harrak et al., "Galacto-Configured Aminocyclitol Phytoceramides are Potent in Vivo Invariant Natural Killer T Cell Stimulators", J. Am. Chem. Soc., 2011, 133(31), 12079-12084, Publication Online: Jul. 5, 2011.

Hintermann, "Recent Developments in Metal-Catalyzed Additions of Oxygen Nucleophiles to Alkenes and Alkynes", Topics in Organomet. Chem., May 2010, 31, 123-155.

Hosokawa et al., "Palladium(II)_catalyzed Oxidation of Carbon-Carbon double bonds of Allylic Compounds with Molecular Oxygen; Regioselective Formation of Aldehydes", J. Chem. Soc., Chem. Commun., 1991, 21, 1559-1560.

Hoover et al., "A Highly Practical Cooper(I)/TEMPO Catalyst System for Chemoselective Aerobic Oxidation of Primary Alcohols", J. Am. Chem. Soc. 2011, 133, 16901-16910.

Hudson et al., "Nosteroidal 2,3-Dihydroquinoline Glucocorticoid Receptor Agonists with Reduced PEPCK Activation", Bioorg. Med. Chem. Lett., 2011, 21(6), 1654-1657.

Hull et al., "Mechanism of Benzoquinone-Promoted Palladium-Catalyzed Oxidative Cross- Coupling Reactions", J. Am. Chem. Soc., 131(28), 2009, 9651-9653, Publication Online: Jul. 1, 2009.

Ito et al., "Induction of Apoptosis in Leukemic Cells by Homovanillic Acid Derivative, Capsaicin, Through Oxidative Stress", Cancer Research, 2004, 64, 1071.

Jira, "Acetaldehyde from Ethylene- A Retrospective on the Discovery of the Wacker Process", Angew. Chem. Int. Ed., Oct. 2009, 48(48), 9034-9037.

Kharasch et al., "Addition of Carbon Tetrachloride and Chloroform to Olefins", Science, Aug. 3, 1945, 102(2640), 128.

Kissin, "Vanilloid-Induced Conduction Analgesia: Selective, Dose-Dependent, Long-Lasting, with a Low Level of Potential Neurotoxicity", Anesth. Analg., 2008, 107(1), 271-281.

Kwong et al., "A General, Efficient, and Inexpensive Catalyst System for the Coupling of Aryl Iodides and Thiols", Org. Lett., 2002, 4(20), 3517-3520, Publication Online: Sep. 11, 2002.

Lai et al., "Reversal of Regiochemistry of Wacker-Type Reactions Oriented by Heteroatoms", J. Org. Chem., Jun. 1992, 57(12), 3485-3487.

Lee et al., "A Facile and Efficient Synthesis of 4-hydroxy-2,6-cis-tetrahydropyrans via Tandem Cross-Metathesis/Thermal S(N)2' Reaction: Protecting-Group-Free Synthesis of (+/−)-diospongin A.", Org. Lett., 2009, 11(22), 5202-5205.

Liu et al., "Highly Regioselective Pd-Catalyzed Intermolecular Aminoacetoxylation of Alkenes and Evidence for cis-Aminopalladation and SN2 C-0 Bond Formation", J. Am. Chem. Soc., 2006, 128(22), 7179-7181.

Lopez et al., "Regia- and Enantioselective Iridium-Catalyzed Intermolecular Allylic Etherification of Achiral Allylic Carbonates with Phenoxides", J. Am. Chem. Soc., 2003, 125(12),3426-3427, Publication Online: Mar. 4, 2003.

Mahatthananchai et al., "Catalytic Selective Synthesis", Angew. Chem. Int. Ed., Oct. 29, 2012, 51, 10954-10990.

Maity et al., "Efficient and Stereoselective Nitration of Mono- and Disubstituted Olefins with $AgNO_2$ and TEMPO", J. Am. Chem. Soc., 2013, 135(9), 3355-3358.

Martinez et al., "Palladium-Catalyzed Vicinal Difunctionalization of Internal Alkenes: Diastereoselective Synethesis of Diamines", Angew. Chem. Int. Ed., 2012, 51(28), 7031-7034.

Michel et al., "Catalyst-Controlled Wacker-Type Oxidation of Protected Allylic Amines", Angew. Chem. Int. Ed., Sep. 24, 2010, 49, 7312-7315.

Miller et al., "Electrode-Mediated Wacker Oxidation of Cyclic and Internal Olefins", Can. J. Chem., 1992, 70(9), 2485-2490.

Miller, D.G. and Wayner, D.D., "Improved Method for the Wacker Oxidation of Cyclic and Internal Olefins", J. Org. Chem., 1990, 55(9), 2924-2927.

Mitsudome et al., "Convenient and Efficient Pd-Catalyzed Regioselective Oxyfunctionalization of Terminal Olefins by Using Molecular Oxygen as Sole Reoxidant", Angew. Chem. Int. Ed., 2006, 45(3), 481-485.

Mitsudome et al., "Convenient and Efficient Pd-Catalyzed Regioselective Oxyfunctionalization of Terminal Olefins by Using Molecular Oxygen as Sole Reoxidant", Angew. Chem. 2006, 118, 495-499.

Mitsudome et al, "Highly Atom-Efficient Oxidation of Electron-Deficient Internal Olefins to Ketones Using a Palladium Catalyst", Angew. Chem. Int. Ed., Apr. 22, 2013, 52, 5961-5964.

Mitsudome et al, "Simple and Clean Synthesis Of Ketones From Internal Olefins Using PdCI2/N,N-dimethylacetamide Catalyst System", Tetrahedron Letters, 54, Jan. 17, 2013, 1596-1598.

Mitsudome et al, "Wacker-Type Oxidation of Internal Olefins Using a PdCI2/N,Ndimethylacetamide Catalyst System under Copper-Free Reaction Conditions", Angew. Chem. Int. Ed., 2010, 49, 1238-1240, published online: Dec. 28, 2009.

Morandi et al, "Regioselective Wacker Oxidation of Internal Alkenes: Rapid Access to Functionalized Ketones Facilitated by Cross-Metathesis", Angew. Chem. Int. Ed., Jul. 26, 2013, 52, 9751-9754.

Mori et al., "Capsaicin, a Component of Red Peppers, Inhibits the Growth of Androgen- Independent, p53 Mutant Prostate Cancer Cells", Cancer Res., Mar. 15, 2006, 66, 3222-3229.

Mukherjee et al., "A Diversity-Oriented Synthesis of Bicyclice cis-Dihydroarenediols, cis-4- Hydroxyscytalones, and Bicyclic Conduritol Analogues", Org. Lett., 2010, 12(11), 2472-2475, Publication Online: May 5, 2010.

Müller et al., "Hydroamination: Direct Addition of Amines to Alkenes and Alkynes", Chem. Rev., 2008, 108(9), 3795-3892, Publication Online: Aug. 26, 2008.

Nagano et al., "Combined Lewis Acid Catalysts in Shotgun Process: A Convenient Synthesis of the Female Sex Pheromone of the Red-Bollworm Moth", Tetrahedron, Oct. 7, 2002, 58(41), 8211-8217.

(56) References Cited

OTHER PUBLICATIONS

Narute et al., "A [Pd]-Mediated w-alkynone ycloisomerization Approach for the Central Tetrahydropyran Unit and the Synthesis of C(31)-C(48) Fragment of Aflastatin A", Org. Biomol. Chem., 2011, 9, 5469-5475.

Piera, J. and Backvall, J.E., "Catalytic Oxidation of Organic Substrates by Molecular Oxygen and Hydrogen Peroxide by Multistep Electron Transfer-A Biomimetic Approach", Angew. Chem. Int. Ed. Apr. 28, 2008, 47, 3506-3523.

Raffier et al., "Desymmetrization of Hepta-1,6-dien-4-ol by Prins Reaction and Subsequent Cross-Metathesis: Access to Diospongine A Homologues", Synthesis, 2011, 24, 4037-4044.

Raghavan et al., "An Efficient Stereoselective Synthesis of Penaresidin A from (E)-2-Protected Amino-3,4-unsatured Sulfoxide", J. Org. Chem., 2010, 75, 748-761, Publication Online: Dec. 21, 2009.

Ritter et al., "A Standard System of Characterization for Olefin Metathesis Catalysts", Organometallics, 2006, 25(24), 5740-5745, Publication Online: Oct. 20, 2006.

Sato et al., "Asymmetric Cyclization of w-Formyl-1,3-Dienes Catalyzed by a Zerovalent Nickel Complex in the Presence of Silanes", J. Org. Chem., 2002, 67(26), 9310-9317.

Seayad et al., "Internal Olefins to Linear Amines", Science, Sep. 6, 2002, 297(5587), 1676-1678.

Sigman et al., "Imparting Catalyst Control Upon Classical Palladium-Catalyzed Alkenyl C-H Bond Functionalization Reactions", Ace. Chem. Res., 2012, 45(6), 874-884.

Smidt et al., "Katalytische Umsetzungen von Olefinen an Platinmetaii-Verbindungen", Angew. Chem. Int., 1959, 71(5), 176-182, with English Abstract.

Stowers et al., "Nitrate as a Redox Co-Catalyst for the Aerobic Pd-Catalyzed Oxidation of Unactivated $sp^3$-C-H Bonds", Chem. Sci., 2012, 3, 3192-3195.

Stahl, S., Cover Picture, Angewandte Chem., 2004, 116, 3480.

Stahl, "Palladium Oxidase Catalysis: Selective Oxidation of Organic Chemicals by Direct Dioxygen-Coupled Turnover", Angew. Chem. Inti. Ed., 2004, 43(26), 3400-3420, Jun. 28, 2004.

Sun et al., "Nonpeptidic and Potent Small-Molecule Inhibitors of ciAP-1/2 and XIAP Proteins", J. Med. Chem, 2010, 53(17), 6361-6367, Publication Online: Aug. 4, 2010.

Trost et al., "Synthetic Strageies to Acetogenins. They hydroxybutenolide Terminus", Tetrahedron Lett., 1995, 36(34), 6021-6024.

Trost, "On Inventing Reactions for Atom Economy", Acc.Chem. Res., 2002, 35(9), 695-705, Publication Online: Mar. 8, 2002.

Tseng et al., "A Modular Synthesis of Salvileucalin B. Structural Domaines", Org. Lett., 2011, 13(16), 4410-4413.

Tsuji et al., "A General Synthetic Method for the Preparation of Metyl Ketones From Terminal Olefins: 2-Decanone", Organic Syntheses, 1984, 62, 9.

Wang et al., "Supercritical Carbon Dioxide and Poly(Ethylene Glycol): An Environmentally Benign Biphasic Solvent System for Aerobic Oxidation of Styrene", Green Chem., 2007, 9, 882-887.

Wang et al., "Palladium-Catalyzed Direct Oxidation of Alkenes with Molecular Oxygen: General and Practical Methods for the Preparation of 1,2-Diols, Aldehydes, and Ketones", J. Org. Chem., 2010, 75(7), 2321-2326.

Wang et al., "A Versatile Catalyst for Reductive Amination by Transfer Hydrogenation", Angew. Chem. Int. Ed., 2010, 49, 7548-7552.

Wang et al., "Pd(II)-Catalyzed Hydroxyl-Directed C-H Activation/C-O Cyclization: Expedient Construction of Dihydrobenzofurans", J. Am. Chem. Soc., 2010, 132(35), 12203-12205, Publication Online: Jan. 10, 2013.

Wenzel, "Oxidation of Olefins to Aldehydes Using A Palladium-Copper Catalyst", J. Chem. Soc., 1993, 862-864.

Wenzel, "Cationic Palladium Nitro Complexes as Catalysts for the Oxygen-based Oxidation of Alkenes to Ketones, and for the Oxydehydrogenation of Ketones and Aldehydes to the Unsaturated Analogues", J. Chem. Soc., Chem. Commun., 1989, 932-933.

Wickens et al., "Aldehyde-Selective Wacker-Type Oxidation of Unbiased Alkenes Enabled by a Nitrite Co-Catalyst", Angew. Chem. Int. Ed., 2013, 52, 11257-11260.

Wickens et al., "Catalyst-Controlled Wacker-Type Oxidation: Facile Access to Functionalized Aldehydes", J. Am. Chem. Soc., 2014, 136, 890-893, Publication Online: Jan. 6, 2014.

Wickens et al., "Catalyst-Controlled Wacker-Type Oxidation: Facile Access to Functionalized Aldehydes", Organic Letters, 2012, 14, 5728-5731.

Zhou et al., "A General and Convenient Catalytic Synthesis of Nitriles from Amides and Silanes", Org. Lett. 2009, 11(11), 2461-2464.

CATALYTIC ANTI-MARKOVNIKOV OXIDATION AND HYDRATION OF OLEFINS

CROSS-REFERENCE TO RELATED APPLICATIONS

This application claims priority under 35 U.S.C. §119(e)(1) to U.S. Provisional Patent Application Ser. Nos. 61/429,061, filed Dec. 31, 2010, 61/490,497, filed May 26, 2011, 61/538,726, filed Sep. 23, 2011, and 61/564,738, filed Nov. 29, 2011, the contents of each of which are incorporated herein by reference in its entirety.

INTRODUCTION

Olefin hydration is an important industrial process for the synthesis of alcohols. The common catalysts used in this transformation are acids, metal oxides, zeolites and clays. However, in these processes, addition of water obeys Markovnikov's rule, and primary alcohols (except ethanol) are difficult to obtain by current hydration methods. Although the indirect protocol involving hydroboration/oxidation affords hydration products with anti-Markovnikov regioselectivity, a stoichiometric amount of relatively expensive borane reagents and a two-step operation are required, during which a large quantity of organic (including organic solvents) and inorganic (boron) waste is generated. Moreover, the peroxides used in the second step (i.e., oxidation) cause safety issues in large-scale production. Given the broad utility of primary alcohols in bulk/fine chemical and the pharmaceutical industry, development of selective catalysts for direct anti-Markovnikov hydration of alkenes is highly desirable, at least in terms of synthetic efficiency, economy and waste reduction.

SUMMARY

In one aspect, the disclosure provides a method for forming an addition product, the method comprising combining a first catalyst, a second catalyst, an oxidant, a reductant, and an olefin reactant in a single reaction vessel to form a reaction mixture, and allowing the reaction mixture to react for a period of time and under conditions suitable to form the addition product.

In some such aspects, the reaction mixture comprises water, and the addition product is a hydration product.

In some such aspects, the olefin reactant is an asymmetric olefin, and wherein the hydration product comprises 50% or more of the anti-Markovnikov hydration product.

In some such aspects, the first catalyst is a metal salt or complex, and wherein the metal is selected from palladium and platinum.

In some such aspects, the second catalyst is a metal hydride, and wherein the metal is selected from ruthenium, rhodium, iron, and iridium.

In some such aspects, the oxidant comprises a first oxidant and an optional co-oxidant.

In some such aspects, the first oxidant is a metal salt, and the co-oxidant is selected from quinone, a substituted quinone, a peroxide, and a metal oxide.

In some such aspects, the reductant is a first alcohol.

In some such aspects, the reaction mixture comprises a second alcohol different from the first alcohol.

In some such aspects, the first catalyst is a metal salt capable of catalyzing the oxidation of a carbon-carbon double bond, and wherein the second catalyst is a metal hydride capable of carrying out the reduction of a carbonyl group.

In some such aspects, the oxidant comprises a metal salt, and wherein the reducing agent comprises an organic alcohol.

In some such aspects, the reactant is a compound comprising an asymmetric olefin.

In some such aspects, the hydration product comprises a primary alcohol and a secondary alcohol, and wherein the ratio of the primary to secondary alcohols is greater than 2:1.

In some such aspects, the allowing the reaction mixture to react comprises catalytically oxidizing an olefin reactant to form an intermediate having the structure of formula (III)

wherein $R^1$, $R^2$, and $R^3$ are independently selected from H, hydrocarbyl, substituted hydrocarbyl, heteroatom-containing hydrocarbyl, substituted heteroatom-containing hydrocarbyl, and functional groups, provided that at least one of $R^1$, $R^2$, and $R^3$ is a non-hydrogen substituent, and further provided that, if $R^3$ is not hydrogen, then both $R^1$ and $R^2$ are non-hydrogen.

In some such aspects, the allowing the reaction mixture to react comprises catalytically reducing the intermediate to form an alcohol having the structure of formula (IV)

wherein $R^1$, $R^2$, and $R^3$ are as defined for formula (III).

In some such aspects, the intermediate is not purified or otherwise isolated prior to the catalytically reducing.

In another aspect, the disclosure provides a method for forming an addition product, the method comprising: (a) catalytically oxidizing an olefin reactant to form an intermediate having the structure of formula (III)

wherein $R^1$, $R^2$, and $R^3$ are independently selected from H, hydrocarbyl, substituted hydrocarbyl, heteroatom-containing hydrocarbyl, substituted heteroatom-containing hydrocarbyl, and functional groups, provided that at least one of $R^1$, $R^2$, and $R^3$ is a non-hydrogen substituent, and further provided that, if $R^3$ is not hydrogen, then both $R^1$ and $R^2$ are non-hydrogen; and (b) catalytically reducing the intermediate to form an alcohol having the structure of formula (IV)

wherein $R^1$, $R^2$, and $R^3$ are as defined for formula (III).

In some such aspects, (a) and (b) are carried out in the same reaction vessel, and wherein the intermediate is not isolated prior to (b).

In another aspect, the disclosure provides a method for forming a product organic alcohol, the method comprising: (a) contacting an olefin reactant containing an asymmetrically substituted olefin with a first catalyst in the presence of a first alcohol to form a carbonyl-containing compound, and reduced first catalyst; (b) contacting the reduced first catalyst with an oxidant to reform the first catalyst; (c) contacting the carbonyl-containing compound with a second catalyst and a second alcohol to form the product organic alcohol and inactivated second catalyst; and (d) contacting the inactivated second catalyst with a reducing agent to reform the second catalyst.

In some such aspects, steps (a) through (d) are performed in one reaction vessel.

In some such aspects, the method is carried out in the presence of water, and wherein the contacting of (a) further produces a product acid.

In some such aspects, the first alcohol is a tertiary alcohol and the second alcohol is a secondary alcohol.

In some such aspects, the inactivated second catalyst is a metal complex.

In some such aspects, the olefin is a terminal olefin, and wherein the organic alcohol comprises a primary alcohol.

In some such aspects, the olefin is a disubstituted terminal olefin, and wherein the organic alcohol comprises a primary alcohol.

In some such aspects, the olefin is a trisubstituted olefin, and wherein the organic alcohol comprises a secondary alcohol.

In some such aspects, the organic alcohol comprises the anti-Markovnikov hydration product of the compound.

In some such aspects, the organic alcohol comprises the anti-Markovnikov and Markovnikov hydration products of the compound in a ratio of at least 2:1.

In some such aspects, the first catalyst is a metal salt or complex, and wherein the metal is selected from palladium and platinum.

In some such aspects, the second catalyst is a second metal hydride, and wherein the metal is selected from ruthenium, rhodium, iron, and iridium.

In some such aspects, the product acid is involved in the reduction that results from (c).

In some such aspects, the oxidant comprises a first oxidant and a co-oxidant.

In some such aspects, the first oxidant is a metal salt, and wherein the metal is selected from copper and iron.

In some such aspects, the co-oxidant is quinone, a substituted quinone, a peroxide, or a metal oxide.

In some such aspects, the contacting of (a), (b), (c), and (d) are carried out in the same reaction vessel.

In another aspect, the disclosure provides a composition comprising: (a) a first catalyst capable of catalyzing an oxidation reaction of an olefin-containing compound; (b) a second catalyst capable of catalyzing a reduction reaction of a carbonyl-containing compound; (c) an oxidant; and (d) a reductant.

In some such aspects, the composition comprises one or more organic solvents, water, or a combination thereof.

In some such aspects, the composition comprises one or more organic alcohols.

In some such aspects, the composition comprises water.

In some such aspects, the composition comprises an olefinic reactant, and the composition is formed by combining the components of a kit with the olefinic reactant, wherein the kit comprises: (a) a first container comprising the first catalyst and the oxidant; and (b) a second container comprising the second catalyst and the reducing agent.

In another aspect, the disclosure provides a kit comprising: (a) a first container comprising a first catalyst capable of catalyzing an oxidation reaction of an olefin-containing compound and an oxidant; and (b) a second container comprising a second catalyst capable of catalyzing a reduction reaction of a carbonyl-containing compound and a reducing agent.

In another aspect, the disclosure provides a method for forming an oxidation product, the method comprising combining a catalyst, an oxidant, a sterically bulky alcohol, and an olefin reactant in a reaction vessel, and allowing the reaction mixture to react for a period of time and under conditions suitable to form the oxidation product.

In some such aspects, the oxidation product comprises an anti-Markovnikov oxidation product and a Markovnikov oxidation product in a ratio of at least 2:1.

In some such aspects, the sterically bulky alcohol is a tertiary alcohol.

In some such aspects, the catalyst is capable of catalyzing an oxidation reaction, and the olefin reactant comprises a terminal olefin.

In some such aspects, the olefin reactant is a terminal olefin, the anti-Markovnikov oxidation product is an aldehyde, and the Markovnikov oxidation product is a ketone.

In some such aspects, the olefin reactant is an asymmetrical trisubstituted (i.e., internal) olefin, the anti-Markovnikov oxidation product is a ketone, and the Markovnikov oxidation product is a ketone.

In some such aspects, the oxidant comprises a first oxidant and a co-oxidant. In other such aspects, the oxidant is a first oxidant only.

These and other aspects will be apparent from the disclosure, including the claims and examples provided herein.

DETAILED DESCRIPTION

Definitions

Figure 1:
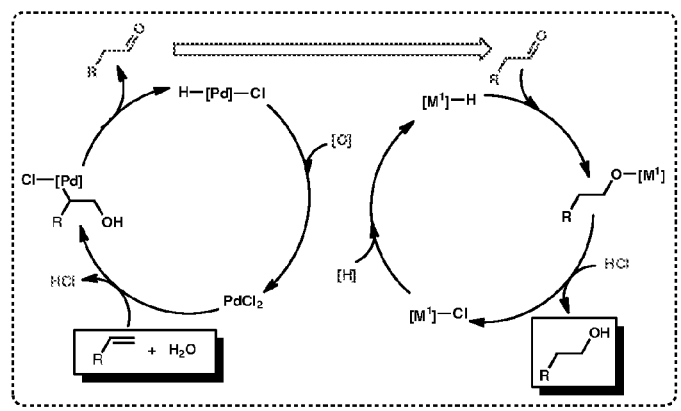
FIG. 1 provides a schematic representation of a double catalytic hydration reaction according to an aspect of the disclosure.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are described herein. It is understood that the present disclosure supersedes any disclosure of an incorporated publication to the extent there is a contradiction.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The term "typically" is used to indicate common practices of the invention. The term indicates that such disclosure is exemplary, although (unless otherwise indicated) not necessary, for the materials and methods of the invention. Thus, the term "typically" should be interpreted as "typically, although not necessarily." Similarly, the term "optionally," as in a material or component that is optionally present, indicates that the invention includes instances wherein the material or component is present, and also includes instances wherein the material or component is not present.

The term "alkyl" as used herein refers to a branched, unbranched or cyclic saturated hydrocarbon group of 1 to about 50 carbon atoms, such as methyl, ethyl, n-propyl, isopropyl, n-butyl, isobutyl, t-butyl, octyl, decyl, tetradecyl, hexadecyl, eicosyl, tetracosyl and the like. Preferred alkyl groups herein may contain 1 to about 36, more typically 1 to 10, carbon atoms. The term "lower alkyl" intends an alkyl group of 1 to 6 carbon atoms, preferably 1 to 4 carbon atoms.

The alkyl groups present on the polymers described herein may be unsubstituted or they may be substituted with one or more substituents including functional groups (e.g., amine, hydroxyl, an olefinic group such as a vinyl or an allyl group), or the like. "Substituted alkyl" refers to alkyl substituted with one or more substituent groups, and this includes instances wherein two hydrogen atoms from the same carbon atom in an alkyl substituent are replaced, such as in a carbonyl group (i.e., a substituted alkyl group may include a —C(=O)— moiety). Other substituents include halogen, ether, hydroxyl, amine functional groups, etc. as defined in more detail below. The terms "heteroatom-containing alkyl" and "heteroalkyl" refer to an alkyl substituent in which at least one carbon atom is replaced with a heteroatom, such as O, S, P, or N, as described in further detail infra. If not otherwise indicated, the terms "alkyl" and "lower alkyl" include linear, branched, cyclic, unsubstituted, substituted, and/or heteroatom-containing alkyl or lower alkyl, respectively.

The term "alkylene" as used herein refers to a difunctional saturated branched or unbranched hydrocarbon chain containing from 1 to 50 carbon atoms. "Lower alkylene" refers to alkylene linkages containing from 1 to 12 carbon atoms, and includes, for example, methylene (—CH$_2$—), ethylene (—CH$_2$CH$_2$—), propylene (—CH$_2$CH$_2$CH$_2$—), 2-methyl-propylene (—CH$_2$—CH(CH$_3$)—CH$_2$—), hexylene (—(CH$_2$)$_6$—) and the like. Similarly, the terms "alkenylene," "alkynylene," "arylene," "alkarylene," and "aralkylene" refer to difunctional (i.e., linking) alkenyl, alkynyl, aryl, alkaryl, and aralkyl groups, respectively.

The term "alkenyl" as used herein refers to a linear, branched or cyclic hydrocarbon group of 2 to about 50 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Generally, although again not necessarily, alkenyl groups herein may contain 2 to about 36 carbon atoms, and for example may contain 2 to 12 carbon atoms. The term "lower alkenyl" intends an alkenyl group of 2 to 6 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively. Similarly, the term "olefin," as in an "olefinic compound" as used herein refers to a mono-unsaturated or di-unsaturated hydrocarbon of 2 to 36 carbon atoms, wherein in some embodiments a carbon-carbon double bond is positioned between the terminal 2 carbon atoms. Olefinic groups within this class are sometimes herein designated as "lower olefinic groups," intending a hydrocarbon containing 2 to 18 carbon atoms containing a single terminal double bond. The latter moieties may also be termed "lower alkenyl." The terms "olefin group," "olefinic group," and "carbon-carbon double bond" are used interchangeably throughout this specification. In some cases, as will be clear from the context, the term "olefin" is used to refer to an olefinic group rather than to a compound containing an olefinic group. In some cases, the olefin group is a part of a silicon-containing compound. Typically, but not necessarily, compounds containing olefinic groups are in a liquid form during use in the methods of the disclosure.

The term "alkynyl" as used herein refers to a linear or branched hydrocarbon group of 2 to 50 carbon atoms containing at least one triple bond, such as ethynyl, n-propynyl, and the like. Generally, although again not necessarily, alkynyl groups herein may contain 2 to about 18 carbon atoms, and such groups may further contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The terms "alkoxy" and "aryloxy" refer to an alkyl group and aryl group, respectively, bound through an oxygen linkage. In some embodiments, the alkyl or aryl group binds through the oxygen linkage to a non-carbon element, such as to a silicon atom. "Lower alkoxy" intends an alkoxy group containing 1 to 10, more preferably 1 to 7, carbon atoms. The terms "oxyalkylene" and "oxyarylene" refer to bifunctional (i.e., linking) alkoxy and aryloxy groups, respectively.

The term "aryl" as used herein refers to an aromatic species having 1 to 3 rings, but typically intends a monocyclic or bicyclic moiety, e.g., phenyl or 1- or 2-naphthyl groups. Optionally, these groups are substituted with 1 to 4, more preferably 1 to 2, substituents such as those described herein, including lower alkyl, lower alkoxy, hydroxyl, amino, and/or nitro. Aryl groups may, for example, contain 6 to 50 carbon atoms, and as a further example, aryl groups may contain 6 to 12 carbon atoms. For example, aryl groups may contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituent, in which at least one carbon atom is replaced with a heteroatom, as will be described in further detail infra. If not otherwise indicated, the term "aryl" includes unsubstituted, substituted, and/or heteroatom-containing aromatic substituents.

The term "aralkyl" refers to an alkyl group with an aryl substituent, and the term "alkaryl" refers to an aryl group with an alkyl substituent, wherein "alkyl" and "aryl" are as defined above. In general, aralkyl and alkaryl groups herein contain 6 to 50 carbon atoms. Aralkyl and alkaryl groups may, for example, contain 6 to 20 carbon atoms, and as a further example, such groups may contain 6 to 12 carbon atoms.

The term "amino" intends an amino group —NR$_2$ where R is hydrogen or an alternative substituent, typically lower alkyl. The term "amino" is thus intended to include primary amino (i.e., NH$_2$), "alkylamino" (i.e., a secondary amino group containing a single alkyl substituent), and "dialkylamino" (i.e., tertiary amino group containing two alkyl substituents).

The term "heteroatom-containing" as in a "heteroatom-containing alkyl group" (also termed a "heteroalkyl" group) or a "heteroatom-containing aryl group" (also termed a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, furyl, pyrimidinyl, imidazolyl, 1,2,4-triazolyl, tetrazolyl, etc., and examples of heteroatom-containing alicyclic groups are pyrrolidino, morpholino, piperazino, piperidino, tetrahydrofuranyl, etc.

"Hydrocarbyl" refers to univalent hydrocarbyl radicals containing 1 to about 50 carbon atoms, including 1 to about 36 carbon atoms, further including 1 to about 18 carbon atoms, and further including about 1 to 12 carbon atoms, including linear, branched, cyclic, saturated and unsaturated species, such as alkyl groups, alkenyl groups, aryl groups, and the like. "Substituted hydrocarbyl" refers to hydrocarbyl substituted with one or more substituent groups, and the term "heteroatom-containing hydrocarbyl" refers to hydrocarbyl in which at least one carbon atom is replaced with a heteroatom such as O, N, P, Si, or S. Unless otherwise indicated, the term "hydrocarbyl" is to be interpreted as including substituted and/or heteroatom-containing hydrocarbyl moieties.

The term "ether" includes both mono and polyethers and refers to groups having a chain containing carbon and oxygen and each of these units consists of 2 to 6 carbons for each oxygen atom. Examples are diethyl and dipropyl ethers, polyethyleneoxide, polyprolyleneoxide, polyethelene glycol, polybuteleneoxide.

"Halo" or "halogen" refers to fluoro, chloro, bromo or iodo, and usually relates to halo substitution for a hydrogen atom in an organic compound.

As used herein, the term "perfluoro," such as a perfluoro group, perfluoro monomer, perfluoro oligomer or perfluoro polymer, refers to a moiety or compound in which fluoro atoms substitute for hydrogen atom completely or almost completely. In some embodiments of perfluoro groups, the hydrogen atoms on between 1 and 3 carbons at a terminus or at a terminal bonding site (i.e., where the group attaches to a substrate or to another chemical moiety) are not replaced with fluoro atoms. Perfluoro groups further include polycarbon or polyether chains having the hydrogen atoms replaced with fluoro atoms.

The terms "halocarbyl" and "halocarbon" refer to hydrocarbyl groups (as defined above) for which one or more hydrogen radicals are replaced with halo radicals. Similarly, the term "perhalocarbyl" refers to hydrocarbyl groups for which all hydrogen radicals are replaced with halo radicals. The terms "halocarbyl" and "halocarbon" include perhalocarbyl, and further includes fluorocarbyl groups, perfluorinated hydrocarbyl groups, chlorocarbyl groups, perchlorinated hydrocarbyl groups, bromocarbyl groups, perbrominated hydrocarbyl groups, iodocarbyl groups, and periodinated hydrocarbyl groups. Similarly, the term "haloether" refers to an ether group in which one or more hydrogen radicals are replaced with halo radicals, and the term "perhaloether" refers to an ether in which all hydrogen radicals are replaced with halo radicals. The term "haloether" includes perhaloethers, unless otherwise specified.

By "substituted" as in "substituted hydrocarbyl," "substituted alkyl," "substituted aryl," and the like, as alluded to in some of the aforementioned definitions, is meant that in the hydrocarbyl, alkyl, aryl, or other moiety, at least one hydrogen atom bound to a carbon (or other) atom is replaced with one or more non-hydrogen substituents. Examples of such substituents include, without limitation, functional groups and the hydrocarbyl moieties $C_1$-$C_{24}$ alkyl (including $C_1$-$C_{18}$ alkyl, further including $C_1$-$C_{12}$ alkyl, and further including $C_1$-$C_6$ alkyl), $C_2$-$C_{24}$ alkenyl (including $C_2$-$C_{18}$ alkenyl, further including $C_2$-$C_{12}$ alkenyl, and further including $C_2$-$C_6$ alkenyl), $C_2$-$C_{24}$ alkynyl (including $C_2$-$C_{18}$ alkynyl, further including $C_2$-$C_{12}$ alkynyl, and further including $C_2$-$C_6$ alkynyl), $C_5$-$C_{30}$ aryl (including $C_5$-$C_{20}$ aryl, and further including $C_5$-$C_{12}$ aryl), and $C_6$-$C_{30}$ aralkyl (including $C_6$-$C_{20}$ aralkyl, and further including $C_6$-$C_{12}$ aralkyl). By "functional group" is meant a group that contains one or more reactive moieites. Examples of functional groups include halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), halocarbonyl (—CO)—X where X is halo, $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO—), carbamoyl (—(CO)—NH$_2$), mono-substituted $C_1$-$C_{24}$ alkylcarbamoyl (—(CO)—NH($C_1$-$C_{24}$ alkyl)), di-substituted alkylcarbamoyl (—(CO)—N($C_1$-$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano (—C≡N), isocyano (—N+≡C—), cyanato (—O—C≡N), isocyanato (—O—N≡C—), isothiocyanato (—S≡CN), azido (—N=N+=N—), formyl (—(CO)—H), thioformyl (—(CS)—H), amino (—NH$_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_5$-$C_{20}$ arylamido (—NH—(CO)-aryl), imino (—CR=NH where R=hydrogen, $C_1$-$C_{24}$ alkyl, $C_5$-$C_{20}$ aryl, $C_6$-$C_{20}$ alkaryl, $C_6$-$C_{20}$ aralkyl, etc.), alkylimino (—CR=N(alkyl), where R=hydrogen, alkyl, aryl, alkaryl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O—), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O—)$_2$), phosphinato (—P(O)(O—)), phospho (—PO$_2$), and phosphino (—PH$_2$), mono- and di-($C_1$-$C_{24}$ alkyl)-substituted phosphino, and mono- and di-($C_5$-$C_{20}$ aryl)-substituted phosphino. In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl and aryl" is to be interpreted as "substituted alkyl and substituted aryl."

It will be appreciated by those of skill in the art that many of the preceding definitions overlap in scope and are not meant to be mutually exclusive. Accordingly, any particular chemical group may fall within more than one of the above-provided definitions.

Unless otherwise specified, reference to an atom is meant to include isotopes of that atom. For example, reference to H is meant to include 1H, 2H (i.e., D) and 3H (i.e., T), and reference to C is meant to include $^{12}$C and all isotopes of carbon (such as $^{13}$C).

In some embodiments, the disclosure provides methods and materials for carrying out a catalytic hydration reaction on a reactant. The product of such reaction includes an organic alcohol, wherein the hydroxy group of the alcohol has been added to the olefin in an anti-Markovnikov fashion. In some embodiments, the overall hydration reaction involves a catalytic oxidation and a catalytic reduction reaction, and may therefore be referred to herein as a double catalytic hydration reaction.

In some embodiments, the disclosure provides methods and materials for carrying out a catalytic oxidation of a reactant containing a olefin group. The product of such reaction includes an organic aldehyde and may further contain an organic ketone. In some such embodiments, the aldehyde product is the major product, as described herein.

Olefin Reactant

In some embodiments, the methods of interest involve an olefinic reactant (also referred to herein as a "substrate" or simply as a "reactant") that is an organic compound comprising an asymmetric olefin. By "asymmetric" is meant that the two substituents attached to one of the olefinic carbons are not the same as the two substituents attached to the other olefinic carbon. In some embodiments, the olefin reactant contains a terminal olefin (such reactants may be referred to simply as "terminal olefins"). By "terminal" is meant that one of the olefinic carbons has two hydrogen atoms, and therefore no carbon atoms, as substituents. In other embodiments, the olefin reactant contains a non-terminal olefin, meaning that both olefinic carbons have at least one non-hydrogen substituent. In some such embodiments, the olefin reactant is a tri-substituted olefin containing three non-hydrogen substituents.

The substituents suitable for the olefin reactant include a wide variety of chemical moieties. In some embodiments, the olefin reactant contains one (or more) aryl substituent(s). Such aryl substituents include single aryl rings as well as annulated ring systems containing 2, 3, 4, or more aryl rings. Such aryl substituents also include aryl rings that contain one or more heteroatoms, such as 2 or 3 heteroatoms, wherein such heteroatoms are selected from N, S, and O. Such aryl substituents also include aryl rings that are substituted with or more substituents. In some such embodiments, the substituents on the aryl ring may be additional aromatic groups or alkyl groups, or mixtures thereof. Thus, for example, the aryl substituent may be heteroaryl, substituted aryl, or substituted heteroaryl. In some embodiments, the aryl substituent further contains one or more substituents, which may be attached at the ortho, meta, and/or para position relative to the olefin of the olefin reactant. In some such embodiments the substituents are electron donating (i.e., activating, such as alkyl, alkoxy, etc. groups). In other such embodiments the substituents are electron activating (i.e., deactivating, such as halo, halo-substituted alkyl, nitro, carbonyl, etc. groups). Combinations of such groups may also be present.

In some embodiments, the olefin reactant contains an alkyl substituent. In some such embodiments, the alkyl substituent may be further substituted and/or may be heteroatom-containing.

In some embodiments, the olefin reactant contains a substituent that is a combination of aryl and alkyl moieties. For example, aralkyl and alkaryl substituents are suitable substituents. In one such embodiment the olefin reactant comprises an allyl group attached to a further chemical moiety such as an aryl group, substituted aryl group, or heteroaryl group.

In some embodiments, the olefin reactant is multiply substituted and contains a combination of alkyl and aryl substituents. For example, the olefin reactant is tri-substituted, wherein the three substituents are independently selected from alkyl and aryl substituents.

In some embodiments, the olefin reactant has the structure of formula (I)

$$(R^1)(R^2)C=C(H)(R^3) \tag{I}$$

wherein $R^1$, $R^2$, and $R^3$ are independently selected from H, hydrocarbyl, substituted hydrocarbyl, heteroatom-containing hydrocarbyl, substituted heteroatom-containing hydrocarbyl, and functional groups, provided that at least one of $R^1$, $R^2$, and $R^3$ is a non-hydrogen substituent, and further provided that, if $R^3$ is not hydrogen, then both $R^1$ and $R^2$ are non-hydrogen.

For example, in some embodiments $R^1$, $R^2$, and $R^3$ are selected from H, alkyl, substituted alkyl, heteroatom-containing alkyl, substituted heteroatom-containing alkyl, alkenyl, substituted alkenyl, heteroatom-containing alkenyl, substituted heteroatom-containing alkenyl, alkynyl, substituted alkynyl, heteroatom-containing alkynyl, substituted heteroatom-containing alkynyl, aryl, heteroaryl, substituted aryl, substituted heteroaryl, and the like.

For example, in some embodiments $R^1$, $R^2$, and $R^3$ are selected from H, aryl, substituted aryl, and aralkyl. In some embodiments, $R^3$ is H. In some embodiments, $R^2$ and $R^3$ are H.

First Catalyst

In some embodiments, the methods of interest involve a first reaction referred to herein as the "oxidation reaction." The oxidation reaction involves contacting the olefin reactant with a first catalyst (also referred to herein as an "oxidation catalyst"). The first catalyst and the conditions under which it is contacted with the olefin reactant are effective to catalyze the oxidation reaction of the olefin reactant.

In some such embodiments, the oxidation reaction is a Wacker-type oxidation and can be carried out under Wacker-type conditions, such as the conditions described in Muzart, *Tetrahedron* v. 63 (2007) pp. 7505-7521 (incorporated herein by reference) and other relevant literature. The oxidation reaction is not limited, however, to a Wacker-type oxidation reaction mechanism. Any suitable mechanism may be used to explain the products obtained via the methods of interest.

In some embodiments, the first catalyst is a metal catalyst, such as a metal salt and/or a metal complex. For example, the metal may be selected from palladium and platinum. Suitable salts of such metals include chloride and bromide salts. The first catalyst may include metal coordinating ligands such as nitrile ligands (e.g., acetonitrile, benzonitrile, etc.), azoline ligands (e.g., oxadiazoline, etc.), and the like. Specific catalyst examples include palladium chloride, palladium acetate, palladium nitrate, and the Lewis base adducts thereof (e.g., $PdCl_2(MeCN)_2$, $PdCl_2(PhCN)_2$, $PdClNO_2(MeCN)_2$, etc.).

Oxidation Reaction

As stated above, in some embodiments, the oxidation reaction involves contacting the olefin reactant with the first catalyst under conditions effective to cause oxidation of the olefin reactant.

The oxidation of the olefin reactant results in the formation of oxidized reactant and reduced first catalyst (also referred to as "inactivated first catalyst").

In some embodiments, the oxidation reaction occurs and is carried out in the presence of an alcohol. In some embodiments, the alcohol is a sterically bulky alcohol. In some such embodiments, the alcohol is sterically more bulky than a secondary alcohol such as i-PrOH. Examples of sterically bulky alcohols are tertiary alcohols, t-butyl alcohol, adamantanol, trimethylsilanol, and the like, as well as derivatives thereof.

Without wishing to be bound by theory, it is believed that the oxidized reactant is a vinyl ether which has incorporated the alcohol present in the reaction. Furthermore, due to the steric bulk of the alcohol, the vinyl ether is the product that minimizes steric interactions of the transition state. Thus, the vinyl ether has the oxygen attached to the least substituted olefinic carbon. In the case of terminal olefin reactants, then, the vinyl ether is a linear vinyl ether with the ether oxygen attached to the unsubstituted olefinic carbon.

In some embodiments, the oxidized reactant is a vinyl ether that has the structure of formula (II)

$$(R^1)(R^2)C\!=\!C(R^3)(OR^4) \quad\quad\quad (II)$$

wherein $R^1$, $R^2$, and $R^3$ are as defined above for formula (I), and wherein R4 is an alkyl group. In some embodiments, R4 is a substituted alkyl such as a branched alkyl. In some embodiments, R4 is t-butyl.

Hydrolysis Reaction

As stated above, and without wishing to be bound by theory, it is believed that the oxidation reaction results in a vinyl ether. As noted below, in some embodiments, the oxidation reaction generates an acid as a byproduct. For example, when palladium chloride is used as the first catalyst, the oxidation reaction generates hydrochloric acid.

In some embodiments, the oxidation reaction is carried out in the presence of water. Under such conditions, the oxidized reactant undergoes hydrolysis and converts from a vinyl ether to a carbonyl-containing compound. In some embodiments, the carbonyl-containing compound is an aldehyde. In other embodiments, the carbonyl-containing compound is a ketone.

In some embodiments, the carbonyl-containing compound has the structure of formula (III)

$$(R^1)(R^2)(H)C\!-\!C(\!=\!O)(R^3) \quad\quad\quad (III)$$

wherein $R^1$, $R^2$, and $R^3$ are as defined above for formula (I). For example, in some embodiments, R3 is H. In other embodiments, none of $R^1$, $R^2$, and $R^3$ is H.

Oxidant

The methods of interest involve an oxidant. In some embodiments, the oxidant is added at the beginning of the hydration reaction and is present throughout the reaction. The oxidant oxidizes the reduced first catalyst to regenerate the first catalyst. Thus, the oxidant is reduced in the reaction with the reduced first catalyst.

In some embodiments, the oxidant is selected from solids, liquids, and gases, and includes materials such as metal halides, metal oxides, peroxides, organic oxidants, and the like. Suitable metals include copper, chromium, osmium, and iron. Examples of metal salts and metal oxides include copper chloride, chromium oxide (e.g., chromium trioxide, chromate and permanganate salts, etc.), manganese oxide (e.g., $MnO_2$), silver oxide, and osmium tetroxide. Examples of peroxides include hydrogen peroxide, benzoyl peroxide, and the like. Examples of organic oxidants include quinone, substituted quinones (1,4-benzoquinone, etc.), 2,2'-dipyridyldisulfide, and the like. In some embodiments, the oxidant is selected from liquids, including acids such as nitric acid, sulfuric acid, and the like. In some embodiments, the oxidant is selected from gases such as oxygen (or an oxygen-containing gas such as air), ozone, fluorine, chlorine, and the like.

In some embodiments, the oxidant is a combination of compounds that, in combination, provide oxidation of the reduced first catalyst. Examples of co-oxidants include combinations of any two, three, or more of the oxidants listed above.

The overall theorized mechanism for the oxidation reaction is shown in the left-hand cycle of FIG. 1.

Second Catalyst

In some embodiments, the methods of interest involve a second reaction referred to herein as the "reduction reaction."

The reduction reaction involves contacting the carbonyl-containing compound (e.g., the aldehyde product that results from hydrolysis of the vinyl ether in the oxidation reaction) with a second catalyst (also referred to herein as a "reduction catalyst" or "transfer hydrogenation catalyst"). The reduction reaction may, in some embodiments, be referred to as a transfer hydrogenation reaction. The second catalyst and the conditions under which it is contacted with the carbonyl-containing compound are effective to catalyze a reduction reaction on the carbonyl group of the carbonyl-containing reactant.

In some embodiments, the second catalyst is a metal catalyst. In some embodiments, the metal is selected from ruthenium, rhodium, iron, iridium, and the like. In some embodiments, the second catalyst is a metal hydride, such as metal hydrides of ruthenium, rhodium, etc. The metal hydride may further include metal coordinating ligands such as diamines, phosphines, carbenes, carbon monoxide, cyclopentadienes, and the like. Some examples of ligands include triphenylphosphine, BINAP, DAIPEN, DPEN, N-heterocyclic carbenes, benzene and benzene derivatives, cyclopentadiene and cyclopentadiene derivatives, and the like. In some embodiments, the catalyst is a transfer hydrogenation catalysts such as those known in the art.

Specific catalyst examples include Shvo's catalyst (1-Hydroxytetraphenylcyclopentadienyl-(tetraphenyl-2,4-cyclopentadien-1-one)-μ-hydrotetracarbonyldiruthenium(II)), Noyori-type catalysts (e.g., bisphosphine RuCl2 diamine catalysts), and the like, including catalysts having the structure of formula (C1) or (C2):

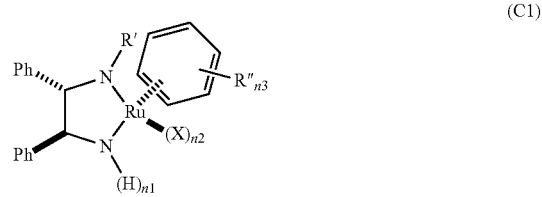

(C1)

(C2)

In formula (C1):

n1 is 1 or 2;

n2 is 0 or 1;

n3 is an integer from 0 to 4;

X is a halogen atom (e.g., Cl, Br);

R' is —SO2-R, wherein R is selected from aryl (e.g., p-methylphenyl) and alkyl (e.g., methyl); and R" is selected from alkyl (e.g., methyl, ethyl, n-propyl, i-propyl, n-butyl, t-butyl, etc.).

For example, in some embodiments of formula (C1), n1 is 1, n2 is 0, n3 is 2; R' is tosyl, and the two R" groups are selected from alkyl groups. For example, the aryl ring coordinated to the Ru center is 1-methyl-4-isopropyl.

In formula (C2), the phosphine ligands and amine ligands are each taken together as bidentate ligands. Examples of bidentate phosphine and amine ligands include

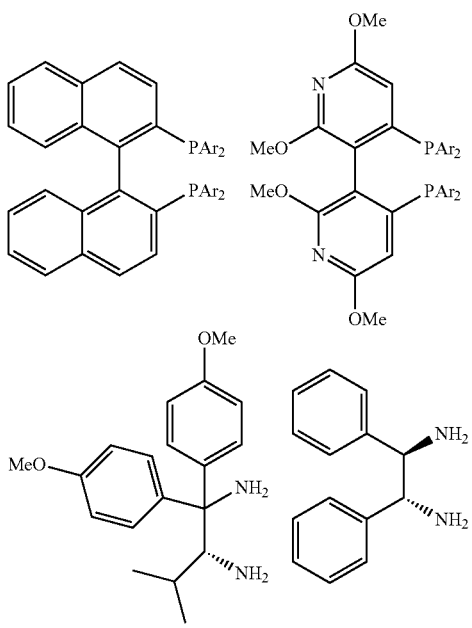

In the above formulae, Ar is selected from phenyl and substituted phenyl rings. Examples of substituted phenyl rings include p-methylphenyl and 3,5-dimethylphenyl.

Reduction Reaction

The reduction of the carbonyl-containing compound results in the formation of an alcohol product and inactivated second catalyst. In some embodiments, and without wishing to be bound by theory, it is believed that the inactivated second catalyst is a metal complex of the second catalyst. Alternatively or in addition, in some embodiments (again not wishing to be bound by theory), the inactivated second catalyst is an oxidized form of the second catalyst. For example, in some embodiments the inactivated second catalyst is a chloride or other halide salt of the second catalyst.

It is believed that the reduction reaction consumes acid. Such acid can be the same acid that is generated in the oxidation reaction, as described above. Accordingly, in some embodiments, the double catalytic hydration reaction as a whole is neutral with respect to the production or consumption of acid. In some embodiments, the acid consumed in the reduction reaction is an acid that is added to the reaction, such as with a buffer material.

Reductant

The methods of interest involve a reducing agent, also referred to as a reductant. In some embodiments, the reductant is added at the beginning of the hydration reaction and is present throughout the reaction. The reductant reduces the inactivated second catalyst to regenerate the second catalyst. Thus, the reductant is oxidized in the reaction with the inactivated second catalyst.

In some embodiments, the reductant is an alcohol. In some embodiments, the reductant is a secondary alcohol, such as isopropyl alcohol. Other reducing agents are known and may be employed as suitable.

Other Components

In some embodiments, the methods of interest involve additional components such as solvents, pH buffers, salts, diagnostic aids, and the like.

A solvent may be present during the double catalytic hydration reaction. In some embodiments, the solvent is an alcohol or a combination of alcohols. For example, in some embodiments, the solvent is a combination of a secondary alcohol (e.g., isopropanol) and a tertiary alcohol (e.g. t-butyl alcohol). In some such embodiments the secondary alcohol further functions as a reductant as described above. Furthermore, in some such embodiments, the tertiary alcohol also serves as a reactant in the oxidation reaction and is incorporated into the product vinyl ether. Other solvents (including solvents that are not active and involved in the hydration reaction) may also be used in the reactions of interest.

In some embodiments, water, acid, or both is/are added and is/are present during the reaction. As mentioned previously, water is involved in the oxidation of the olefin reactant. Also as mentioned previously, acid is generated and consumed in the overall double catalytic hydration.

For example, the reaction can be carried out in a buffered aqueous solution, with the pH regulated to acidic conditions. In some embodiments, acid is present in the reaction as a byproduct of either the reduction or oxidation reactions, as described herein. Whether added or generated in situ, water and acid are present in sufficient quantity to catalyze the catalytic formation of the alcohol product.

Amounts of the Reactants

The absolute and relative amounts of the various components mentioned above will vary, for example, according to the reaction conditions and the identities of the olefin reactant and other compounds involved in the reaction.

In some embodiments, the first catalyst is present in an amount between about 0.1 and 30 mol % relative to the amount of olefin reactant. For example, the first catalyst may be present between about 0.5 and 20 mol %, or between about 1 and 15 mol %. In some embodiments, the first catalyst is present in about 30 mol % or less, or about 25 mol % or less, or about 20 mol % or less, or about 15 mol % or less, or about 10 mol % or less.

In some embodiments, the second catalyst is present in an amount between about 0.1 and 30 mol % relative to the amount of olefin reactant. For example, the second catalyst may be present between about 0.5 and 20 mol %, or between about 1 and 15 mol %. In some embodiments, the second catalyst is present in about 30 mol % or less, or about 25 mol % or less, or about 20 mol % or less, or about 15 mol % or less, or about 10 mol % or less.

In some embodiments, water is present (e.g., added) in an amount between about 1 and 100 equivalents relative to the amount of olefin reactant. For example, water is present between about 1 and 10 equivalents, or between about 1 and 2 equivalents. In some embodiments, water is present in about 100 equivalents or less, or about 50 equivalents or less, or about 10 equivalents or less, or about 2 equivalents or less, or about 1.5 equivalents or less, or about 1.1 equivalents or less.

In some embodiments, the oxidant is present in an amount between about 100 and 200 mol %, or more than 200 mol % relative to the amount of olefin reactant. For example, the second catalyst may be present in about 100 mol % or more, or about 120 mol % or more, or about 150 mol % or more. In embodiments where a dual oxidant/co-oxidant system is used, these amounts refer to the total amount of oxidant (i.e., the sum of the oxidant and co-oxidant). For example, in some embodiments one oxidant is present in an amount of about 10 to 50 mol %, and the co-oxidant is present in an amount of about 50 to 90 mol %. The reductant can be present in similar amounts, such as between 100 and 200 mol %, or in an amount more than 200 mol % relative to the amount of olefin reactant. It will be appreciated that, where the oxidant is used as a solvent as well (e.g., using an alcohol or mixture of alcohols, as described herein), the oxidant(s) may be present in significantly more than 200 mol % relative to the amount of olefin reactant.

Products

In some embodiments, the methods of interest provide alcohol products. In the hydration reaction of an asymmetric olefin reactant, the anti-Markovnikov hydration product is the product that results when the hydroxyl group attaches to the less substituted of the olefinic carbons. Thus, when the olefin reactant is a terminal olefin, the anti-Markovnikov product is a primary alcohol.

In some embodiments, the product is exclusively (within the limits of detection) the anti-Markovnikov product. In some embodiments, the product is a mixture of anti-Markovnikov and Markovnikov products, in a ratio within the range of about 1:2 to 100:1, or within about 1:1 to 50:1. For example, the ratio of anti-Markovnikov to Markovnikov products is 1:1.5 or more, or 1:1 or more, or 2:1 or more, or 3:1 or more, or 4:1 or more, or 5:1 or more, or 10:1 or more, or 15:1 or more, or 20:1 or more, or 50:1 or more.

Furthermore, in some embodiments the crude yield of anti-Markovnikov product (i.e., prior to purification) is about 50% or greater (based on the amount of olefin reactant at the beginning of the reaction), or about 60% or greater, or about 70% or greater, or about 80% or greater, or about 90% or greater, or about 95% or greater.

In some embodiments, the alcohol product has the structure of formula (IV)

$$(R^1)(R^2)(H)C—C(H)(OH)(R^3) \quad (IV)$$

wherein $R^1$, $R^2$, and $R^3$ are as defined above for formula (I). For example, in some embodiments, R3 is H. In other embodiments, none of $R^1$, $R^2$, and $R^3$ is H.

In some embodiments, the methods of interest provide aldehyde products. As indicated herein, the aldehyde product can be the intermediate in the production of the alcohols described herein. Alternatively, the methods of interest can be carried out specifically for the purpose of generating aldehydes. In such embodiments, reaction conditions are altered accordingly. For example, in some such embodiments, the second catalyst and/or reductant described above is/are not added to the reaction. In some such embodiments, the product of the reaction is an aldehyde corresponding to anti-Markovnikov oxidation, and may further contain the ketone corresponding to Markovnikov oxidation, as exemplified in the following equation:

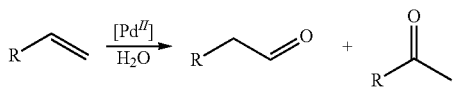

wherein R is selected from aryl (including heteroaryl, substituted aryl, and substituted heteroaryl) and alkyl (including heteroatom containing alkyl, substituted alkyl, and substituted heteroatom-containing alkyl). In some such embodiments, the selectivity of the reaction in forming the aldehyde over the ketone product is 50% or greater, or 60% or greater, or 70% or greater, or 80% or greater, or 90% or greater, or 95% or greater, or 98% or greater or 99% or greater. For example, the product is a mixture of an aldehyde (i.e., anti-Markovnikov oxidation product) and a ketone (i.e., Markovnikov oxidation product) in a ratio of 2:1 or greater, or 3:1 or greater, or 4:1 or greater, or 5:1 or greater, or 10:1 or greater.

Mechanism and Methods

Figure 2:
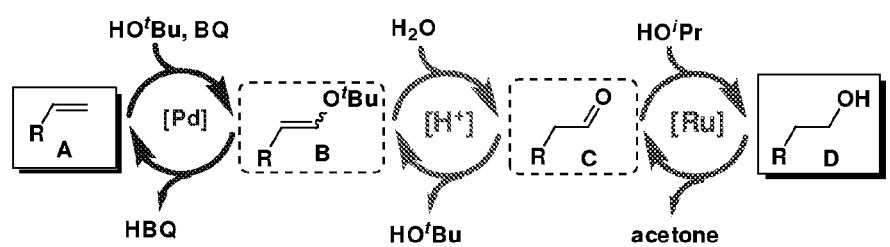
FIG. 2 provides a further schematic representation of a double catalytic hydration reaction according to an aspect of the disclosure.

Without wishing to be bound by theory, in some embodiments it is believed that a triple relay catalysis system operates in this formal anti-Markovnikov olefin hydration process. An embodiment of the triple relay system is shown in FIG. 2. In the presence of t-BuOH the olefin reactant (A) undergoes Pd-catalyzed oxidation to generate t-Butyl vinyl ether (B). Due to the bulkiness of t-BuOH, the linear vinyl ether is preferred, which ultimately provides the high anti-Markovnikov selectivity. During such a Wacker-like process, acids are generated (HCl and hydroquinone). Subsequently, in the presence of water, vinyl ether B converts to aldehyde C through acid-catalyzed hydrolysis. Finally, aldehyde C is reduced to primary alcohol D via a Ru-catalyzed transfer-hydrogenation reaction. Based on this proposed mechanism, it will be apparent that the t-BuOH component can be replaced with any bulky compound capable of adding to the olefin group in the olefin reactant. Examples of such are provided herein.

In some embodiments, the hydration reactions of interest are one-pot methods for converting asymmetric olefins into alcohols with anti-Markovnikov selectivity. By "one-pot" is meant that the asymmetric olefin is combined with all necessary reactants to form the desired product in the same reaction vessel—no transfer and/or isolation of intermediate compounds is necessary. The hydration reactions involve two or more catalytic reactions that occur sequentially. The reactants for each catalytic reaction are provided to a single reaction vessel. Accordingly, the reactants are selected such that the reactants for one catalytic reaction do not interfere with the other catalytic reaction.

In some embodiments, the oxidation reactions of interest are one-pot methods for converting asymmetric olefins into oxidation products with anti-Markovnikov selectivity. The oxidation reactions involve a bulky alcohol that forms a vinyl ether intermediate. For terminal olefin reactants, the oxidation product is an aldehyde. For non-terminal asymmetric olefins, the oxidation product is a ketone that is the anti-Markovnikov product.

The sequential nature of the hydration reactions of interest mean that one or more intermediate compounds are formed, which intermediate compounds including the vinyl ether and the carbonyl-containing compound described herein. Such intermediate compounds can be isolated, if desired. That is, the hydration reactions of interest can be carried out in sequential order in multiple reaction vessels with product isolation procedures used for intermediates. In some embodiments, however, no isolation of the intermediate compounds is carried out.

The methods of interest may further include appropriate purification and isolation steps to remove impurities and reactants from the product alcohol. Furthermore, where the product alcohol contains a mixture of anti-Markovnikov and Markovnikov products, the product may be purified to remove the undesired addition product.

In some embodiments, the methods of interest are suitable for preparation of alcohols on any desired scale, including reparatory/research scale and industrial scale. Thus, the reaction vessel in which the methods are carried out may be of any convenient size, such as from microliter scale to multi-liter (5-, 10-, 100-liters or greater) scale.

Reaction times and reaction conditions (e.g., temperature, atmosphere, etc.) will vary and may be determined by reference to the examples and disclosure provided herein, as well as routine experimentation and consultation of the relevant literature when necessary. For example, reaction times may vary between 10 min and 24 hours, or between 30 min and 12 hours, or between 1 and 6 hr. In some embodiments, reaction temperatures are elevated, such as about 30° C. or greater, or 35° C. or greater, or 50° C. or greater, or 70° C. or greater, or 90° C. or greater, or 100° C. or greater. In some embodiments, reaction temperatures are kept at 100° C. or lower, or 70° C. or lower, or 50° C. or lower, or 35° C. or lower.

It is to be understood that while the invention has been described in conjunction with the preferred specific embodiments thereof, that the foregoing description and the examples that follow are intended to illustrate and not limit the scope of the invention. It will be understood by those skilled in the art that various changes may be made and equivalents may be substituted without departing from the scope of the invention, and further that other aspects, advantages and modifications will be apparent to those skilled in the art to which the invention pertains.

EXAMPLES

Materials and Methods: All reactions unless otherwise specified were carried out in a Vacuum Atmospheres Glovebox under a nitrogen atmosphere. All substrates were passed through a column of basic alumina prior to usage except for 1-octene, which was distilled over $CaH_2$ before being passed through a column of basic alumina under a nitrogen atmosphere. $PdCl_2(MeCN)_2$ was prepared following literature procedures. Benzoquinone was recrystallized from i-PrOH prior to usage. Shvo's catalyst [1-Hydroxytetraphenyl-cyclopentadienyl(tetraphenyl-2,4-cyclopentadien-1-one)-μ-hydrotetracarbonyldiruthenium(II)] was purchased from Strem and $CuCl_2$ from Aldrich. Both were used as received. $H_2O$ was distilled under argon. Anhydrous i-PrOH from Aldrich was freeze-pump-thawed three times under argon and anhydrous t-BuOH also from Aldrich, was degassed, before use. $^1H$ and $^{13}C$ NMR spectra were recorded on a Varian 500 Mhz, Varian 400 Mhz or a Varian 300 Mhz spectrometer. High resolution mass spectra were provided by the California Institute of Technology Mass Spectrometry Facility using JEOL JMS-600H High Resolution Mass Spectrometer. GC-MS data was also provided through the California Institute of Technology Mass Spectrometry Facility using HP 5970 series MSD with HP 5890 GC.

Gas chromatography data was obtained using an Agilent 6850 FID gas chromatograph equipped with a HP-5 (5%-phenyl)-methylpolysiloxane capillary column (Agilent). Instrument conditions-inlet temperature: 250° C.; detector temperature: 250° C.; hydrogen flow: 30 ml/min; air flow: 400 ml/min; constant col+makeup flow: 25 ml/min. Method: 50° C. for 2 min., followed by a temperature increase of 10° C./min to 115° C., hold for 0.5 min., another temperature increase of 1° C./min. to 125° C., hold for 0.5 min., then a temperature increase of 5° C./min to 140° C., hold 0.5 min. and a final temperature increase of 60 C/min to 300° C. and hold at 300° C. for 5 min. (total run time=30.67 min). Response factors were collected for styrene (1a), 2-phenylethanol (2a), ethylbenzene (3a), 1-phenylethanol (4a), phenylacetaldehyde (5a) and acetophenone (6a) following literature procedures.

Condition A: Procedure for hydration of styrene (for [styrene]=0.25 M): $PdCl_2(MeCN)_2$ (0.01 mmol, 0.0026 g), Shvo's catalyst (0.01 mmol, 0.0109 g), $CuCl_2$ (0.02 mmol, 0.0027 g) and benzoquinone (0.08 mmol, 0.0088 g) were weighed into a 1 dram vial in the glovebox, followed by the addition of i-PrOH (0.2 ml) and t-BuOH (0.2 ml). Styrene (0.1 mmol, 11.5 μl) was added to the mixture followed by addition of $H_2O$ (0.11 mmol, 2 μl). The resulting mixture was stirred in the glovebox at 85° C. for 6 h. GC sample preparation: Tridecane (0.00123 mmol, 3 μl) was added to the reaction mixture as an internal standard. The mixture was then diluted with diethylether (3 ml) and ca. 0.5 ml of the resultant mixture was filtered through a plug of silica gel followed by flushing with ethyl acetate (ca. 1 ml). GC retention times (min) were as follows: ethylbenzene 3a (5.31), styrene 1a (5.80), phenylacetaldehyde 5a (8.37), 1-phenylethanol 4a (8.67), acetophenone 6a (8.75), 2-phenylethanol 2a (9.62) and tridecane (14.35).

Condition B: Procedure for hydration of other substrates (for [substrate]=0.125 M): $PdCl_2(MeCN)_2$ (0.04 mmol, 0.0104 g), Shvo's catalyst (0.04 mmol, 0.0436 g), $CuCl_2$ (0.08 mmol, 0.0108 g) and benzoquinone (0.32 mmol, 0.0352 g) were weighed into a 20 ml vial in the glovebox, followed by the addition of i-PrOH (1.1 ml) and t-BuOH (2.2 ml). The substrate (0.4 mmol) was added to the mixture followed by addition of $H_2O$ (0.4 mmol, 8.1 μl). After the resulting mixture was stirred in the glovebox at 85° C. for 6 h, it was diluted with pentane (6 ml) and filtered through a plug of silica gel followed by flushing with ethyl acetate (6 ml). The solvent was removed under vacuum, and the desired primary alcohol product was purified via a standard silica gel flash chromatography.

Condition C: Procedure for hydration of other substrates (for [substrate]=0.067 M): $PdCl_2(MeCN)_2$ (0.04 mmol, 0.0104 g), Shvo's catalyst (0.04 mmol, 0.0436 g), $CuCl_2$ (0.08 mmol, 0.0108 g) and benzoquinone (0.4 mmol, 0.0432 g) were weighed into a 20 ml vial in the glovebox, followed by the addition of i-PrOH (2 ml) and t-BuOH (4 ml). The substrate (0.4 mmol) was added to the mixture followed by addition of $H_2O$ (0.4 mmol, 8.1 μl). After the resulting mixture was stirred in the glovebox at 85° C. for 6 h, it was diluted with pentane (6 ml) and filtered through a plug of silica gel followed by flushing with ethyl acetate (6 ml). The solvent was removed under vacuum, and the desired primary alcohol product was purified via a standard silica gel flash chromatography.

Condition D: Procedure for hydration of 1-octene (for [1-octene]=0.067 M): $PdCl_2(MeCN)_2$ (0.04 mmol, 0.0104 g), Shvo's catalyst (0.04 mmol, 0.0436 g), $CuCl_2$ (0.08 mmol, 0.0108 g) and benzoquinone (0.4 mmol, 0.432 g) were weighed into a 20 ml vial in the glovebox, followed by the addition of i-PrOH (3 ml) and t-BuOH (3 ml). 1-octene (0.4 mmol, 62.8 μl) was added to the mixture followed by addition of $H_2O$ (0.4 mmol, 8.1 μl). After the resulting mixture was stirred in the glovebox at 85° C. for 6 h, it was diluted with pentane (6 ml) and filtered through a plug of silica gel followed by flushing with ethyl acetate (6 ml). The solvent was removed under vacuum, and purification of the alcohol products were attempted via a standard silica gel flash chromatography.

Procedure for hydration of allylalcohol and 3-buten-1-ol: $PdCl_2(MeCN)_2$ (0.01 mmol, 0.0026 g), Shvo's catalyst (0.01 mmol, 0.0109 g), $CuCl_2$ (0.02 mmol, 0.0027 g) and benzoquinone (0.1 mmol, 0.0108 g), dppf (3 μmol, 0.0018 g) were weighed into a 1 dram vial in the glovebox, followed by the addition of i-PrOH (0.18 ml) and t-BuOH (1.8 ml). The substrate (0.1 mmol) was added to the mixture and the resulting mixture was stirred in the glovebox at 85° C. for 65 h. 1,3-propanediol: $^1H$ NMR ($CDCl_3$): 3.87 (t), 1.83 (p). 1,4-butanediol $^1H$ NMR ($CDCl_3$): 3.63 (t), 1.65 (m). GC sample preparation: Tridecane (0.00123 mmol, 3 μl) was added to the reaction mixture as an internal standard. The mixture was then diluted with diethylether (3 ml) and ca. 0.5 ml of the resultant mixture was filtered through a plug of silica gel followed by flushing with ethyl acetate (ca. 1 ml). GC retention times were as follows: 1,3-propanediol (4.84), 1,4-butanediol (6.70).

Example 1

Styrene Oxidation

This study focused on the effect of additional metal salts on the reactivity and selectivity of Wacker-type oxidation and styrene was used as the model substrate. All reactions were conducted under a nitrogen atmosphere and $PdCl_2(PhCN)_2$ (10 mol %) was employed as the initial Pd oxidant. As illustrated in Scheme 1, Ru salt is not only compatible with the Pd-mediated oxidation, but has a positive effect on the yield and product selectivity (entry 2). When $CuCl_2$ was used as the stoichiometric oxidant, catalyst turnover was observed, and the selectivity (aldehyde vs ketone) can be achieved as high as 5.4:1 (entry 3). Addition of silver salts did not have positive effect (entries 4 and 5).

Scheme 1. Effects of additional metal salts on the aldehyde-selective Wacker-type oxidant

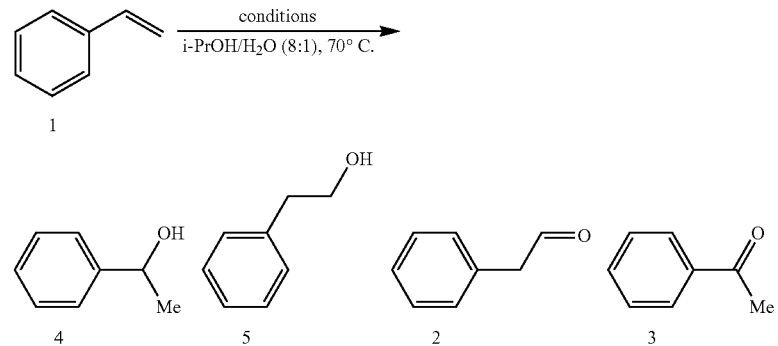

| Entry | Additives | Yield (2)[a] | Yield (3)[a] | Selectivity (2/3) |
|---|---|---|---|---|
| 1 | none | 3.4% | 1.5% | (2.2:1) |
| 2 | $RuCl_3$ hydrate (10 mol %) | 7.1% | 1.9% | (3.7:1) |
| 3 | $RuCl_3$ hydrate (10 mol %) $CuCl_2$ (30 mol %) | 20% | 3.7% | (5.4:1) |
| 4 | $RuCl_3$ hydrate (10 mol %) $AgSF_6$ (20 mol %) | 8.1% | 3.6% | (2.2:1) |
| 5 | $RuCl_3$ hydrate (10 mol %) $CuCl_2$ (30 mol %) $AgSF_6$ (20 mol %) | 19% | 3.9% | (4.9:1) |

[a]Yields are determined by gas chromatography

To investigate compatibility, i-PrOH was used as the stoichiometric reductant because it is cheap, safe to use, and environmentally benign; and $CuCl_2$ (30 mol %) was tentatively used as the oxidant (Scheme 2). When $RuCl_3$ was used as the co-catalyst, no alcohol product was observed (entry 1); however, upon switching to Shvo's catalyst, the primary alcohol (phenyl ethanol) was isolated as the major product (13.5% yield) with good selectivity (entry 2). When styrene was treated with the oxidation conditions first then with Shvo's catalyst and i-PrOH after 8 h, no alcohol product was detected and the aldehyde (2) was the major product (entry 3).

Scheme 2. Studies on Compatibility

| Entry | Conditions | Yields (4 | 5 | 2 | 3)[a] |
|---|---|---|---|---|---|
| 1 | $PdCl_2(PhCN)_2$ (10 mol %) $RuCl_3$ hydrate (10 mol %) $CuCl_2$ (30 mol %) | 0% | 0% | 19.2% | 2.5% |
| 2 | $PdCl_2(PhCN)_2$ (10 mol %) Shvo's catalyst (8 mol %) $CuCl_2$ (30 mol %) | 3% | 13.5% | 0% | 1.2% |

| | -continued | | | | |
|---|---|---|---|---|---|
| 3 | PdCl$_2$(PhCN)$_2$ (10 mol %)<br>RuCl$_3$ hydrate (10 mol %) CuCl$_2$ (30 mol %) in THF<br>after 10 h, then Shvo's catalyst (8 mol %) in i-PrOH | 0% | 0% | 21% | 5.2% |

[a]Yields are determined by gas chromatography

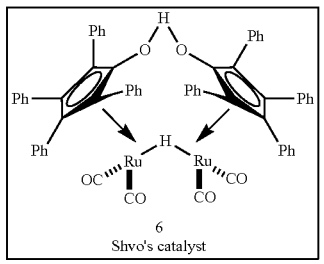

6
Shvo's catalyst

Control experiments were subsequently conducted to understand the role of each reactant (Scheme 3). In the absence of water, almost no reaction occurred (entry 1); in the absence of i-PrOH, only oxidation products were observed, suggesting i-PrOH is the source of reductant (entry 2). Similar results were observed without use of Shvo's catalyst (entry 3). Pd plays a role in providing reactivity (entry 4). Without CuCl$_2$, only a trace of amount alcohol or ketone products were detected and a large amount of over reduction product (ethyl benzene) was formed, which was only observed in a trace of amount when CuCl$_2$ was present. The role of Cu(II) salt may prevent the formation of metal-dihydride species that may account for the hydrogenation of the olefin.

generated from the oxidant cycle would likely be detrimental to the Ru-hydride complex. As further evidence for this, 1 equiv. 4-methyl-2,6-di(t-Butyl)pyridine was added as a base buffer, and alcohol products were isolated in 25% yield with the primary alcohol as the major product albeit in a poorer regioselectivity (entry 2). Use of a less acidic oxidant, such as quinones, was expected to be beneficial; indeed, by switching to benzoquinone (BQ) (0.5 equiv) as the oxidant, both the yield and selectivity was significantly increased (entry 3). However, when using BQ as the solo oxidant, a considerable amount of ethylbenzene was formed as the major byproduct. Knowledge acquired in the control experiments (Scheme 3, entry 5) indicates that even a catalytic amount of Cu(II) can

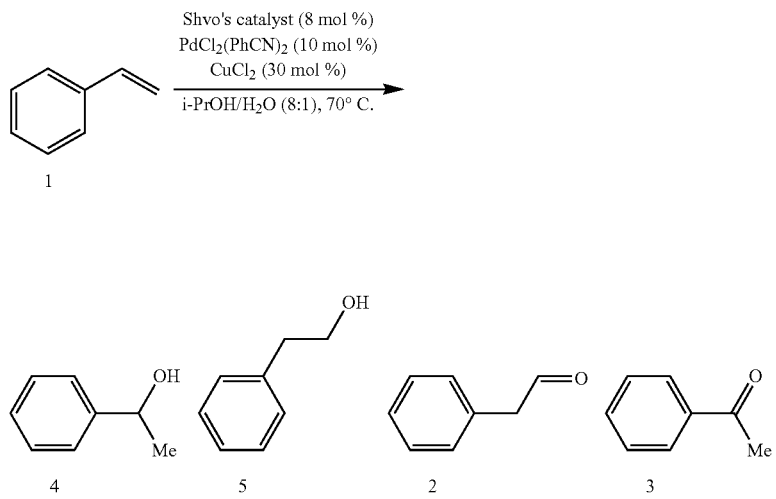

Scheme 3. Control experiments

| Entry | Conditions | Yields (4 | 5 | 2 | 3)[a] |
|---|---|---|---|---|---|
| 1 | no H$_2$O | 0% | 0% | trace | 0.4% |
| 2 | no i-PrOH | 0% | 0% | 21.3% | 5.3% |
| 3 | no Shvo's catalyst | 0% | 0% | 18.7% | 5.9% |
| 4 | no PdCl$_2$(PhCN)$_2$ | 0% | 0% | 0% | trace |
| 5 | no CuCl$_2$ | 0% | trace | 0% | 1.1% |

[a]Yields are determined by gas chromatography

With an understanding of the role of each reactant component, this reaction was further optimized (Scheme 4). Use of a stoichiometric amount of Cu(II) salt almost did not provide any alcohol products (entry 1). A large concentration of HCl avoid such an over-reduction. Use a combination of 20 mol % CuCl$_2$ and 0.5 equiv BQ as mix-oxidants effectively minimized the formation of ethylbenzene and afforded the desired primary alcohol in 51% yield (entry 4).

Scheme 4. Selective optimization experiments

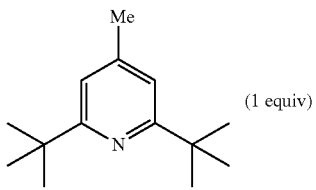

| Entry | Conditions | Yields (4 | 5 | 2 | 3)[a] |
|---|---|---|---|---|---|
| 1 | CuCl$_2$ (1 equiv) | 0% | trace | 23% | 4.8% |
| 2 | CuCl$_2$ (1 equiv), 2,6-di-t-butyl-4-methylpyridine (1 equiv) | 10% 25% yield on alcohols | 15% | 2.1% | 6.8% |
| 3 | BQ (50 mol %) | 2-3% 28-29% yield on alcohols | 26% | 0.38% | 12.8% |
| 4 | CuCl$_2$ (20 mol %), BQ (50 mol %)[b] | 9.6% | 51% | 0.30% | 3.6% |

[a] Yields are determined by gas chromatography
[b] 10 mol % Shvo's catalyst was used Further Studies and Optimization.

Combining both the t-BuOH solvent effect and chloride ligand factor, further enhances the anti-Markovnikov selectivity. For the reduction cycle, a combination of i-PrOH and Shvo's catalyst was selected because i-PrOH can serve as an inexpensive, clean and safe reductant via metal-catalyzed transfer hydrogenation, and Shvo's complex is commonly used as a catalyst for transfer hydrogenation of carbonyl compounds and also known to tolerate aqueous conditions.

Scheme 5. General reaction scheme for styrene hydration to product 2-phenylethanol (2a), ethylbenzene (3a), 1-phenylethanol (4a), phenylacetaldehyde (5a) and acetophenone (6a). BQ: benzoquinone.

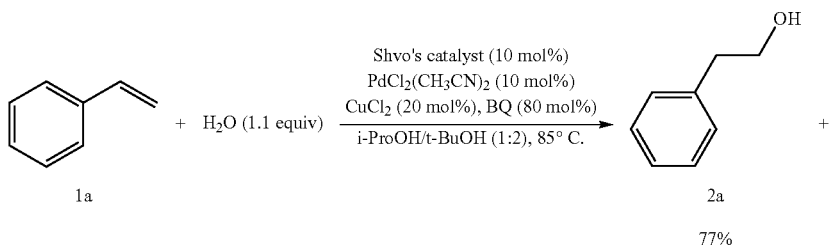

-continued by products

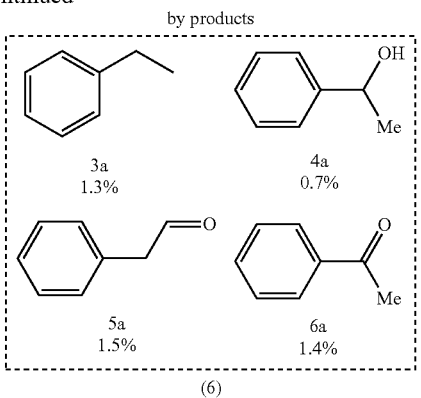

(6)

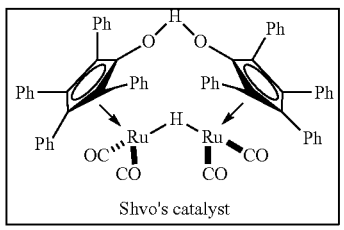

Shvo's catalyst $$\text{Anti-Markovnikov selectivity} = \frac{[1° \text{ alcohol}] + [\text{aldehyde}]}{[2° \text{ alcohol}] + [\text{ketone}]} = 38$$

(7)

Using the conditions shown in Scheme 5, 2-phenylethanol (2a) was obtained in 77% yield with exceptionally high anti-Markovnikov selectivity (38:1). Under the standard conditions, the reaction proceeded with an excellent product selectivity and byproducts (3a to 6a) were all formed in less than 2% yield. The absence of the Pd catalyst shut down the production of oxygenated products completely, although the over-reduction product (ethylbenzene) was still formed in 26% yield. Without Shvo's catalyst, no alcohol products were observed and aldehyde 5a was the major product. $CuCl_2$ was originally intended as a co-oxidant and later appeared to play a critical role in slowing down the over-reduction, as the absence of $CuCl_2$ led to significantly increased yields of ethylbenzene. 1,4-Benzoquinone (BQ) is widely used as a hydrogen acceptor and two-electron oxidant in $Pd^{II}$-catalyzed reactions, and was found to be the best co-oxidant for this transformation, and omission of this component resulted in no alcohol formation. The role of i-PrOH as the reductant was highlighted by formation of aldehyde 5a (57% yield) almost exclusively in its absence. t-BuOH proved to be responsible for enhanced reactivity and selectivity where without t-BuOH, lower yields and regioselectivity of the primary alcohol was obtained. As expected, removal of water from the reaction mixture (using 4 Å Molecular sieves) is detrimental since no oxygenated product was observed under anhydrous conditions. Results are provided in Table 1.

TABLE 1

Studies with styrene as the substrate. The Reaction concentration is 0.25M.
Yields and conversions were determined by GC analysis, using tridecane as the internal standard.
(BQ: 1,4-Benzoquinone; MS: Molecular sieves)*, †

| Entry | Change from the "standard conditions" | Conversion (%) | Yield of 2a (%) | Yield of byproducts (%) | | | |
|---|---|---|---|---|---|---|---|
| | | | | 3a | 4a | 5a | 6a |
| 1 | none | 89 | 77 | 1.3 | 0.7 | 1.5 | 1.4 |
| 2 | no $PdCl_2(CH_3CN)_2$ | 34 | 0 | 26 | 0 | 0 | 0 |
| 3 | no Shvo's catalyst | 80 | 0 | 0.2 | 0 | 42 | 0 |
| 4 | no $CuCl_2$ | >99 | 48 | 32 | 5.9 | 0.5 | 1.4 |
| 5 | no BQ | 58 | 0 | 0.9 | 0 | 0 | 0 |
| 6 | no i-PrOH | 88 | 0 | 0.5 | 0 | 57 | 0 |
| 7 | no t-BuOH | 48 | 18 | 2.0 | trace | trace | trace |
| 8 | no t-BuOH, but 28 equiv $H_2O$ | 75 | 64 | 2.0 | 4.9 | 0.96 | 9.9 |
| 9 | replace $H_2O$ with 4 Å MS | >99 | 0 | 57 | 0 | 0 | 0 |

*The loss of mass balance in entry 5 is unclear but presumably caused by either styrene oligomerization or complexation with metal catalysts.
†The loss of mass balance in entry 6 (57% vs 88%) is presumably caused by the lability of the benzylic α proton and the reactivity of the aldehyde to form oligomers and aldol condensation products.

Example 2

Additional Reactants

The substrate scope was examined on a preparative scale (0.4 mmol, Scheme 6). The primary alcohol products were isolated, purified using silica-gel flash column chromatography and characterized via NMR spectroscopy and High Resolution Mass Spectrometry (HRMS), or identified by comparison of the NMR and Gas chromatography-mass spectrometric (GC-MS) data with the authentic samples. In general, aryl substituted terminal olefins provide good yields of primary alcohols with excellent anti-Markovnikov selectivity (≥20:1). A number of functional groups are tolerated under these reaction conditions, such as alkyl, naphthyl, trifluormethyl and nitro groups as well as various halides. Aliphatic olefins also provided hydration products, despite the challenging nature of these substrates (entries 11 and 12). Although obtaining high regioselectivity for aliphatic substrates is more difficult, these results are promising because under previous (Spencer's) conditions only Markovnikov product was observed for aliphatic substrates. One key merit of this method is that the major stoichiometric byproduct, 1,4-hydroquinone (HBQ) can be easily recovered and converted to BQ in an excellent yield via a facile aerobic oxidation.

Scheme 6. [Pd]/[Ru] catalyzed hydration of functionalized styrenes, 1-octene and allylbenzene.

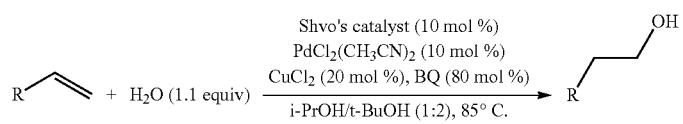

| Entry | Substrate | Product | Yield | Selectivity (1° OH : 2° OH)# |
|---|---|---|---|---|
| 1 | 1a | 2a | 61% (GC yield 65%)*<br>84% (GC yield 83%)‡ | ≥20:1 |
| 2 | 1b | 2b | 42%† | ≥20:1 |
| 3 | 1c | 2c | 61%† | ≥20:1 |
| 4 | 1d | 2d | 60%‡ | ≥20:1 |
| 5<br>6 | 1e | 2e | 72%† | ≥20:1 |
| 7 | 1f | 2f | 75%‡ | ≥20:1 |

Scheme 6. [Pd]/[Ru] catalyzed hydration of functionalized styrenes, 1-octene and allylbenzene.

$$R\text{—}\!=\!\!\text{—} + H_2O\ (1.1\ \text{equiv}) \xrightarrow[\text{i-PrOH/t-BuOH (1:2), 85°C.}]{\substack{\text{Shvo's catalyst (10 mol \%)} \\ \text{PdCl}_2(\text{CH}_3\text{CN})_2\ (10\ \text{mol \%}) \\ \text{CuCl}_2\ (20\ \text{mol \%}),\ \text{BQ}\ (80\ \text{mol \%})}} R\text{—}\!\!\!\diagup\!\!\!\!\diagdown\!\!\text{OH}$$

| Entry | Substrate | Product | Yield | Selectivity (1° OH: 2° OH)[#] |
|---|---|---|---|---|
| 8 | 4-Br-C6H4-CH=CH2 (1g) | 4-Br-C6H4-CH2CH2OH (2g) | 72%[†] | ≥20:1 |
| 9 | 4-F-C6H4-CH=CH2 (1h) | 4-F-C6H4-CH2CH2OH (2h) | 63%[*]<br>84%[‡] | ≥20:1 |
| 10 | 4-O2N-C6H4-CH=CH2 (1i) | 4-O2N-C6H4-CH2CH2OH (2i) | 83%[‡] | ≥20:1 |
| 11 | 3,5-(CF3)2-C6H3-CH=CH2 (1j) | 3,5-(CF3)2-C6H3-CH2CH2OH (2j) | 74%[†] | ≥20:1 |
| 12 | 1-octene (1k) | 1-octanol (2k) | 56%[∥,§] (2k:4k = 1:1.4) | |
|  |  | 2-octanol (4k) | 54%[¶,§] (2k:4k = 1:1.9) | |
|  | allylbenzene (1m) | 3-phenyl-1-propanol (2m) | 12%[‡] (2m)<br>(2m:4m = 1:2.1)[#] | |
|  |  | 1-phenyl-2-propanol (4m) |  |  |

[*]Isolated yield and [C] (initial substrate concentration) = 0.25 M;
[†]Isolated yield and [C] = 0.125 M;
[‡]Isolated yield, [C] = 0.067 M and 1 equiv of BQ was employed;
[§]Attempted purification through column chromatography and yield was determined via $^1$H-NMR using mesitylene as the internal standard;
[∥]i-PrOH:t-BuOH = 1:1 [C] = 0.067 M and 1 equiv of BQ;
[¶]i-PrOH:t-BuOH = 1:2 [C] = 0.067 M and 1 equiv of BQ;
[#]The ratio was determined via $^1$H-NMR analysis of the crude reaction mixture.

Example 3

Mechanistic Studies

A number of experiments were conducted to examine the reaction mechanism. See Scheme 7. In the absence of water, i-PrOH and Shvo's catalyst, a mixture of vinyl t-butyl ether geometric isomers 7 and aldehyde 5a were observed by $^1$H-NMR spectroscopy and GC-MS, providing evidence for the proposed t-butyloxypalladation pathway (eq 7). When i-C$_3$H$_7$OD and t-C$_4$H$_9$OD were used, mono- and di-deuterium incorporation was observed at the β-position, supporting a proton-mediated enol ether hydrolysis pathway, although deuteration via an aldehyde-enol tautomerization after the aldehyde formation cannot be ruled out (eq 8). Regular H$_2$O was used because it only constitutes 0.14% by volume and undergoes rapid H/D exchange with deuterated alcohols. When i-C$_3$D$_7$OD and t-C$_4$H$_9$OD were used instead, 87% deuterium incorporation at the α-position was observed as well, strongly supporting an i-PrOH mediated transfer hydrogenation mechanism (eq 9).

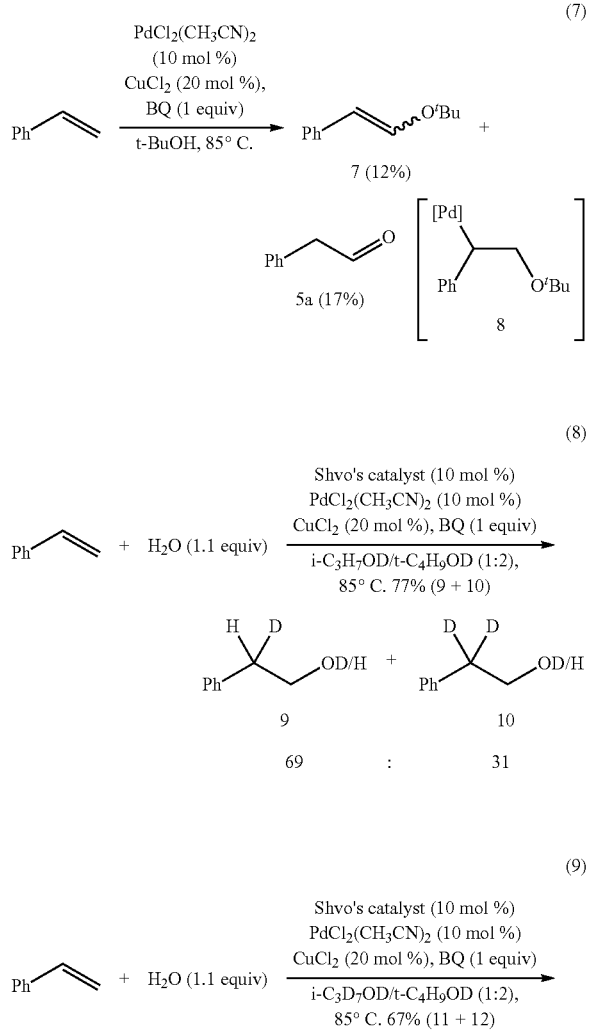

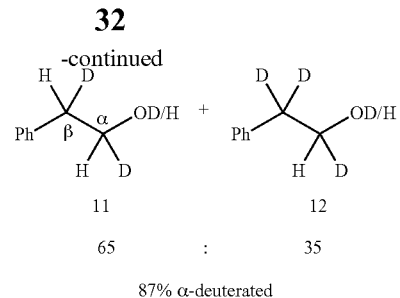

Example 4

Characterization Data

Except 2-(3,5-bis(trifluoromethyl)phenyl)ethanol (2j), all the alcohol products are either known compounds or commercially available. $^1$H NMR and HRMS data were provided for all the primary alcohol compounds. We further checked the $^{13}$C NMR data of known compounds 2a, 2b, 2c, 2e, and 2g. Full characterization data was provided for compound 2j.

2-phenethanol (2a): 41 mg, 84% yield. $^1$H NMR (500 MHz, CDCl$_3$) δ 7.35-7.29 (m, 2H), 7.27-7.21 (m, 3H), 3.86 (t, J=6.6 Hz, 2H), 2.88 (t, J=6.6 Hz, 2H); $^{13}$C NMR (126 MHz, CDCl$_3$) δ 138.46, 129.02, 128.58, 126.47, 63.67, 39.20; HRMS (EI+) calcd for C$_8$H$_{10}$O 122.0732. found 122.0730.

2-(4-(tert-butyl)phenyl)ethanol (2b): 30 mg, 42% yield. $^1$H NMR (400 MHz, CDCl$_3$) δ 7.35 (d, J=8.1 Hz, 2H), 7.17 (d, J=8.1 Hz, 2H), 3.86 (t, J=6.4 Hz, 2H), 2.85 (t, J=6.5 Hz, 2H), 1.32 (s, 9H); $^{13}$C NMR (101 MHz, CDCl$_3$) δ 149.30, 135.27, 128.66, 125.47, 63.66, 38.61, 34.38, 31.34; HRMS (EI+) calcd for C$_{12}$H$_{18}$O 178.1361. found 178.1358.

2-(4-methylpehenyl)ethanol (2c): 33 mg, 61% yield. $^1$H NMR (400 MHz, CDCl$_3$) δ 7.13 (s, 2H), 3.84 (t, J=6.5 Hz, 2H), 2.84 (t, J=6.6 Hz, 2H), 2.33 (s, 2H); $^{13}$C NMR (101 MHz, CDCl$_3$) δ 136.18, 135.41, 129.44, 129.05, 63.94, 38.91, 21.17; HRMS (EI+) calcd for C$_9$H$_{12}$O 136.0886. found 136.0888

2-(2-Naphthyl)ethanol (2d): 41 mg, 60% yield. $^1$H NMR (300 MHz, CDCl$_3$ 7.84-7.76 (m, 3H), 7.69 (s, 1H), 7.51-7.41 (m, 2H), 7.37 (d, J=8.3 Hz, 1H), 3.96 (brs, 2H), 3.05 (t, J=6.5 Hz, 2H), 1.42 (s, 1H); HRMS (EI+) calcd for C$_{12}$H$_{12}$O 172.0888. found 172.0892.

2-(2-methylpehenyl)ethanol (2e): 39 mg, 72% yield. $^1$H NMR (300 MHz, CDCl$_3$) δ 7.21-7.09 (m, 4H), 3.85 (t, J=6.6 Hz, 2H), 2.90 (t, J=6.9 Hz, 2H), 2.34 (s, 3H), 1.49-1.35 (m, 1H); $^{13}$C NMR (126 MHz, CDCl$_3$) δ 136.65, 136.56, 130.57, 129.75, 126.74, 126.19, 62.78, 36.53, 29.84, 19.58; HRMS (EI+) calcd for C$_9$H$_{12}$O 136.0888. found 138.0888.

2-(4-chlorophenyl)ethanol (2f): 46.3 mg, 60% yield. $^1$H NMR (300 MHz, CDCl$_3$) δ 7.31-7.26 (m, 2H), 7.20-7.14 (m, 2H), 3.85 (q, J=6.3 Hz, 2H), 2.84 (t, J=6.5 Hz, 2H), 1.36 (t, J=5.6 Hz, 1H); HRMS (EI+) calcd for C$_8$H$_9$ClO 156.0342, found 156.0340.

2-(4-bromophenyl)ethanol (2g): 58 mg, 72% yield. $^1$H NMR (300 MHz, CDCl$_3$) δ 7.43 (d, J=8.3 Hz, 2H), 7.11 (d, J=8.4 Hz, 2H), 3.83 (t, J=6.5 Hz, 2H), 2.82 (t, J=6.5 Hz, 2H); $^{13}$C NMR (126 MHz, CDCl$_3$) δ 137.69, 131.74, 130.89, 120.44, 63.50, 38.66; HRMS (EI+) calcd for C$_8$H$_9$BrO 199.9839. found 199.9837.

2-(4-fluorophenyl)ethanol (2h): 47 mg, 84% yield. $^1$H NMR (300 MHz, CDCl$_3$) δ 7.23-7.15 (m, 2H), 7.05-6.95 (m, 2H), 3.85 (t, 6.3 Hz, 2H), 2.85 (t, J=6.5 Hz, 2H); HRMS (EI+) calcd for C$_8$H$_9$FO 140.0638. found 140.0637.

2-(4-nitrophenyl)ethanol (2i): 55.4 mg, 83% yield. $^1$H NMR (300 MHz, CDCl$_3$) δ 8.15 (d, J=8.7 Hz, 2H), 7.38 (d, J=8.7 Hz, 2H), 3.90 (dd, J=6.5, 4.8 Hz, 2H), 2.95 (t, J=6.4 Hz, 2H), 1.40 (t, J=4.7 Hz, 1H); HRMS (EI+) calcd for C$_8$H$_9$NO$_3$ 167.0582. found 167.0590.

2-(3,5-bis(trifluoromethyl)phenyl)ethanol (2j): 87 mg, 84% yield. R$_f$: 0.3 (30% ethyl acetate in hexane); $^1$H NMR (300 MHz, CDCl$_3$) δ 7.76 (d, J=8.4 Hz, 1H), 7.71 (s, 2H), 3.94 (t, J=6.3 Hz, 2H), 3.00 (t, J=6.3 Hz, 2H); $^{13}$C NMR (126 MHz, CDCl$_3$) δ 141.54, 131.80 (q, J=33.2 Hz), 129.35, 123.50 (q, J=272.7 Hz), 120.72-120.54 (m), 62.90, 38.71; $^{19}$F NMR (282 MHz, CDCl$_3$) δ −62.87; IR (NaCl plate) 3382 (br), 2919, 2849, 1995, 1624, 1461, 1278, 1137 cm$^{-1}$; HRMS (EI+) calcd for C$_{10}$H$_8$F$_3$O 258.0479. found 258.0487.

1-octanol (2k) and 2-octanol (4k): The yield of compounds 2k and 4k was determined via crude $^1$H NMR using mesitylene as an internal standard by comparing the integration of the α protons of the alcohols with the methyl peaks of mestylene. Purification of compounds 2k and 4k was attempted via silica gel flash chromatography, and a mixture of compounds 2k and 4k with an unknown aromatic impurity was isolated. $^1$H NMR (500 MHz, CDCl$_3$) δ 3.79 (m, 1H, compound 4k) 3.64 (t, J=7.0 Hz, 2H, compound 2k), 1.56 (m, 2H, compound 2k), 1.45-1.28 (CH$_2$ protons for both 2k and 4k), 1.18 (d, J=6.5 Hz, 3H, compound 4k), 0.88 (t, J=6.5 Hz, 3H, for both compounds 2k and 4k); HRMS (M-H) calcd for C$_8$H$_{17}$O 129.1279. found 129.1276. The identity of compound 4m was further confirmed by GC-MS, in which the synthetic sample gave an identical retention time (8.6 min for 4k and 9.9 min for 2k) and mass spec as the authentic sample: for 2k, m/z 129 (M-1), 112, 97, 84, 69, 56, 41; for 2k, m/z 129 (M-1), 115, 97, 84, 69, 55, 45, 41.

3-phenylpropan-1-ol (2m): 6.4 mg, 12% yield. $^1$H NMR (300 MHz, CDCl$_3$) δ 7.33-7.26 (m, 2H), 7.24-7.16 (m, 3H), 3.69 (q, J=6.3 Hz, 2H), 2.72 (t, 6.3 2H), 1.97-1.85 (m, 2H), 1.25 (t, J=5.3 Hz, 1H). HRMS (EI+) calcd for C$_9$H$_{12}$O 136.0888. found 136.0884. The ratio between compounds 2m and 4m was determined via crude $^1$H NMR by comparing the integration of the α protons of the alcohols. Isolation of pure compound 4m was unsuccessful due to contamination of an unknown impurity. The identity of compound 4m was further confirmed by GC-MS, in which the synthetic sample gave an identical retention time (11.1 min) and mass spec as the authentic sample: m/z 136 (M), 121, 117, 103, 92, 91, 77, 65, 51, 45, 39.

Example 5

Recovery of Hydroquinone

PdCl$_2$(MeCN)$_2$ (0.04 mmol, 0.0104 g), Shvo's catalyst (0.04 mmol, 0.0436 g), CuCl$_2$ (0.08 mmol, 0.0108 g) and benzoquinone (0.37 mmol, 0.040 g) were weighed into a 20 ml vial in the glovebox, followed by the addition of i-PrOH (2 ml) and t-BuOH (4 ml). Styrene (46 μL, 0.4 mmol) was added to the mixture followed by addition of H$_2$O (0.4 mmol, 8.1 μl). The resulting mixture was stirred in the glovebox at 85° C. for 6 h. Crude reaction mixture was washed three times with toluene (2 ml) and filtered through a celite plug. The celite plug was subsequently washed with ethyl acetate (ca 5 ml). The ethyl acetate fraction was recombined with the remaining material after the toluene wash. After removal of the solvent, pure hydroquinone was obtained as a white crystal (30 mg, 74% yield). $^1$H NMR (300 MHz, CD$_3$CN) δ 6.64; HRMS (EI+) calcd for C$_6$H$_6$O$_2$ 110.0368. found 110.0390.

Example 6

Synthesis and Characterization of Vinyl Enol Ether

PdCl$_2$(MeCN)$_2$ (0.04 mmol, 0.0104 g), CuCl$_2$ (0.08 mmol, 0.0108 g) and benzoquinone (0.4 mmol, 0.432 g) were weighed into a 20 ml vial in the glovebox, followed by the addition of t-BuOH (6 ml). Styrene (46 μl, 0.4 mmol) was added to the mixture and the resulting mixture was stirred in the glovebox at 85° C. for 6 h. Yield was determined via crude NMR using mesitylene as an internal standard. The olefin peaks for the cis and trans isomers were both observed by crude NMR: $^1$H NMR (300 MHz, CDCl$_3$) trans isomer: δ 7.02 (d, J=12.4 Hz, 1H), 5.99 (d, J=12.4 Hz, 1H); cis isomer 6.45 (d, J=7.1 Hz, 1H), 6.45 (d, J=5.24 Hz, 1H). The ratio between trans and cis isomers is 1.5:1. This data fits with previously reported values for these vinyl enol ethers. GC/HRMS was additionally employed to characterize the compounds ([C$_{12}$H$_{16}$O] cald 176.1201. found 176.1216).

Example 7

Labeling Studies

Synthesis of deuterated products 9 and 10: General procedure (styrene as the substrate, Condition C) was followed using i-C$_3$H$_7$OD and t-butanol-OD. Deuterated 2-phenylethanol products were isolated by silica gel chromatography as an inseparable mixture of 9 and 10. The yield (77%) was determined via GC using response factors calculated for 2a relative to tridecane. $^1$H NMR (300 MHz, CDCl$_3$) δ 7.35-7.29 (m, 2H), 7.27-7.21 (m, 3H), (m, J=6.6 Hz, 2H), 2.88 (m, 0.68H). HRMS HRMS (EI+) calcd for C$_8$H$_8$OD$_2$ 124.0857. found 124.0860; calcd for C$_8$H$_9$OD 123.0794. found 123.0796. Integration analysis indicates the β-position incorporated one deuterium in 69% of the product and two deuterium atoms in 31% of the product. This calculation approximates that no 2a was formed.

Synthesis of deuterated products 11 and 12: General procedure (styrene as the substrate, Condition C) was following using i-propanol-d8 and t-butanol-OD. Deuterated 2-phenylethanol products were isolated by silica gel chromatography as an inseparable mixture. The yield (67%) was determined via GC using response factors calculated for 2a relative to tridecane. $^1$H NMR (300 MHz, CDCl$_3$) δ 7.35-7.29 (m, 2H), 7.27-7.21 (m, 3H), (m, J=6.6 Hz, 1.13H), 2.88 (m, 0.65H). Integration analysis indicates the α position incorporated one deuterium in 87% of the product and the β position incorporated one deuterium in 65% of the product and two deuterium atoms in 35% of the product. These calculation approximates that no 2a was formed. Both compounds 11 and 12 do not get ionized on HRMS (EI+). GC-MS spectrum indicates a single peak matched the retention time with compound 2a, but shows a mass of m/z 124 and 125 along with m/z 123 as a minor peak (the m/z 122 peak was only observed marginally).

Example 8

Hydration of 1-octene 1-octene (0.2 mmol, 31.4 μL), PdCl$_2$(MeCN)$_2$ (0.02 mmol, 0.0052 g), Shvo's catalyst (0.02 mmol, 0.0218 g), tert-butyl-1,4-benzoquinone (0.3 mmol, 0.0503 g), CuCl$_2$ (0.02 mmol, 0.0027 g), 1 μL t-BuOH/H$_2$O mixture (2:1) were stirred together for 12 h at 35° C. 1 μL of the t-BuOH/H$_2$O mixture (2:1) was added every 30 min up to 4 h. 2,4-dimethylpentanol (1 mmol, 142.5 μL) was added to the mixture and the mixture stirred at 85° C. for 16 h. The product yield and selectivity were determined by gas chromatography. 1-octanol was isolated by column chromatography and characterized by $^1$H NMR. A 34% GC yield of 1-octanol was obtained at a selectivity of 20:1 anti-Markonikov:Markonikov (95%). The method and results are shown in Scheme 8 below.

Scheme 8.

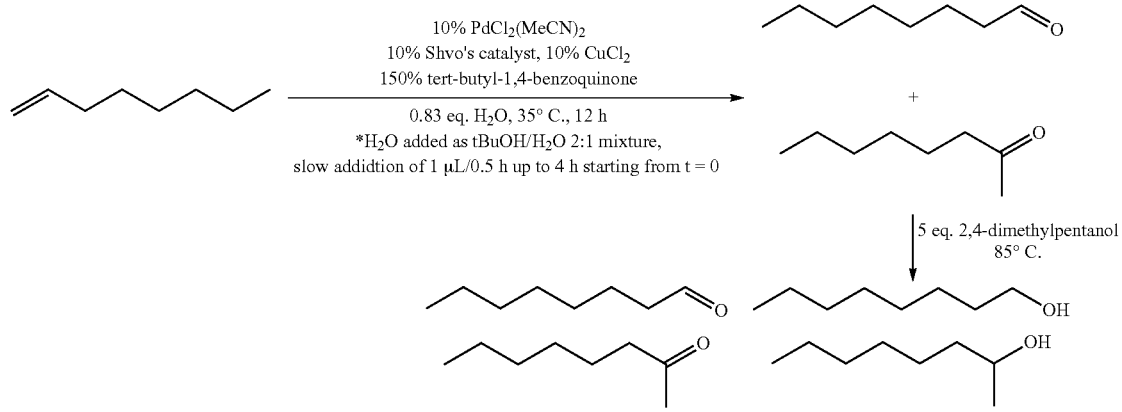

Example 9

Preparation of Aldehydes

Summary. PdCl$_2$(MeCN)$_2$ is used as the oxidation catalyst with p-benzoquinone (BQ) as reoxidant and t-BuOH as solvent in the oxidation of olefins to aldehydes. For oxidation of aromatic olefins such as styrene and ring-substituted styrenes, the reaction is carried out at 85° C. using a 0.125 M solution under aerobic conditions. For oxidation of aliphatic olefins such as 1-octene, the reaction is carried out at 35° C. in a 0.083 M solution with 5% CuCl$_2$ as co-oxidant on top of BQ and PdCl$_2$(MeCN)$_2$ as catalyst in t-BuOH solvent. See Scheme 9. Styrene and 1-octene reactions are monitored via gas-chromatography and selectivity is obtained by integrating the peaks corresponding to the aldehyde and ketone in the chromatogram. For all other olefins, selectivity is obtained by integrating the methylene protons' peak (for aldehyde) and methyl protons' peak (for ketone) in the $^1$H NMR spectrum, of the crude reaction mixture. All aldehyde and ketone products are isolated by converting them to the corresponding hydrazones using 2,4-dinitrophenylhydrazine in ethanol/H$_2$O/H$_2$SO$_4$ mixture and purified using silica gel column chromatography.

Scheme 9.

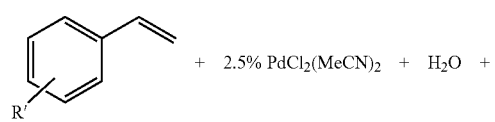 + 2.5% PdCl$_2$(MeCN)$_2$ + H$_2$O +

(2)

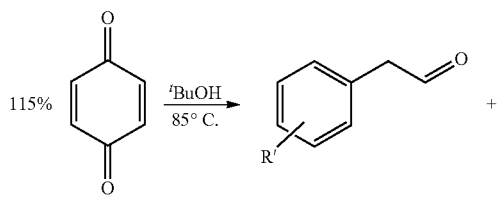

R' = H (2), C$_n$H$_{2n+1}$, Cl, Br, F, CF$_3$, NO$_2$, CO$_2$Me (3)

R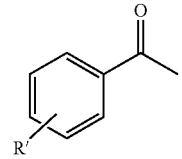 + 10% PdCl$_2$(MeCN)$_2$ + 1.1 H$_2$O + 5% CuCl$_2$ +

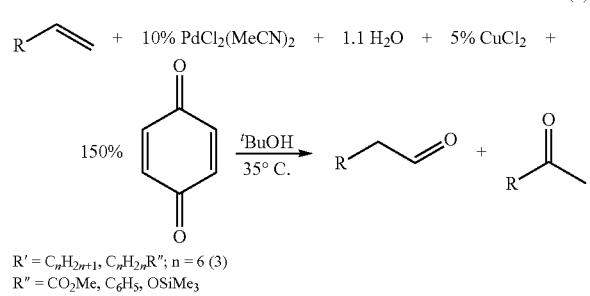

R' = C$_n$H$_{2n+1}$, C$_n$H$_{2n}$R"; n = 6 (3)
R" = CO$_2$Me, C$_6$H$_5$, OSiMe$_3$

General procedure: All olefin oxidation reactions were carried out under aerobic conditions. All liquid olefins are filtered through a plug of basic alumina prior to usage, except for 1-octene, which is distilled over CaH$_2$ before being filtered through a plug of basic alumina. 2,4-dinitrophenylhydrazine solution is prepared following literature procedures.

GC sample preparation: Tridecane (0.00123 mmol, 3 μl) was added to the reaction mixture as an internal standard. The mixture was then diluted with diethylether (2 ml) and ca. 0.5 ml of the resultant mixture was filtered through a plug of silica gel followed by flushing with ethyl acetate (ca. 1 ml). GC retention times (min) were as follows: styrene 2 (5.80), phenylacetaldehyde 2a (8.37), acetophenone 2b (8.75), 1-octene 3 (4.12), octanal 3a (7.59), 2-octanone 3b (7.39) and tridecane (14.35).

Example procedure for styrene and other aromatic olefin oxidation. t-BuOH was preheated to 85° C. before being added (4.8 ml) to PdCl$_2$(MeCN)$_2$ (3.9 mg, 15 µmol) and p-benzoquinone (74.7 mg, 0.69 mmol) in a 20 ml glass vial. H$_2$O (12.2 µL, 0.6 mmol) and olefin (0.6 mmol) were then added and the mixture stirred for 60 min at 85° C.

Example procedure for 1-octene and other aliphatic olefin oxidation. t-BuOH was preheated to 35° C. before being added (4.8 ml) to a 20 ml glass vial containing PdCl$_2$ (MeCN)$_2$ (15.6 mg, 0.06 mmol), CuCl$_2$ (4 mg, 0.03 mmol), and p-benzoquinone (97.2 mg, 0.9 mmol). H$_2$O (11.9 µL, 0.66 mmol) and olefin (0.6 mmol) were then added and the mixture stirred for 7 h at 35° C.

Example procedure for isolation of aldehyde. All reaction mixtures are removed from heating and flash-freezed at −78° C. (dry ice/EtOH bath) immediately after reaction and warmed to 30° C. after the mixture is completely frozen. A solution of 2,4-dinitrophenylhydrazine (1.2 eq.) is added to the mixture at 30° C. and the mixture stirred for 1 h at room temperature. H$_2$O (ca. 10 ml) is added to the mixture, stirred for 1 min. and filtered. The residue is washed with cold H$_2$O (ca. 20 ml). The filtrate and aqueous washing is then combined and extracted with methylene chloride five times. The residue is re-dissolved in the organic extract and the solution dried over Na$_2$SO$_4$, followed by removal of solvents. A crude $^1$H NMR is taken with the solid product. The material is purified using silica gel chromatography with 3% ethylacetate in hexanes to obtain the aldehyde hydrazone (c) and ketone hydrazone (d) respectively.

$^1$H NMR data for phenylacetaldehyde-2,4-dinitrophenylhydrazone 2c (80% isolated yield): δ 10.99 (s, 1H), 9.125 (d, 1H, J=2.5 Hz), 8.325 (ddd, 1H, J=10 Hz), 7.97 (d, 1H, J=10 Hz), 7.60 (t, 1H, J=5.5 Hz), 7.38-7.26 (m, 5H), 3.76 (d, 2H, J=5.5 Hz).

Figure 3:
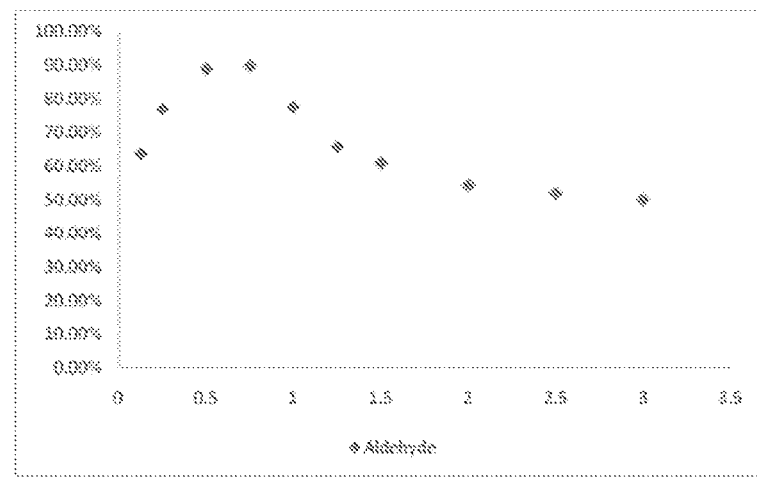
FIG. 3 provides a graph showing aldehyde yield (%) vs. reaction time (h) for the oxidation of styrene according to an embodiment herein.

The oxidation of styrene with PdCl$_2$(MeCN)$_2$ proceeded immediately at 85° C. in t-BuOH solvent (0.125 M) and in the presence of 115% BQ as reoxidant and stoichiometric amounts of H$_2$O (with respect to styrene). An aldehyde yield of 90% was obtained in 60 minutes of reaction along with 2% ketone to give an overall aldehyde selectivity of 98% (aldehyde:ketone 45:1) and TOF of 36 h$^{-1}$ for 2.5 mol % catalyst loading (FIG. 3). A lower catalyst loading of 1% can also be used to give a TOF of 71 h$^{-1}$ but with only 94% selectivity (aldehyde:ketone 15:1). At 1.5% catalyst loading, a TOF of 45 h$^{-1}$ may be achieved with 95% selectivity (aldehyde:ketone 19:1). Clearly, selectivity decreases with catalyst loading although higher turnovers can be achieved with less catalyst. One key merit of our method is that our major stoichiometric by-product, 1,4-hydroquinone (HBQ) can be easily converted back to BQ in an excellent yield via a facile aerobic oxidation. A wide variety of functional groups are well-tolerated by our catalytic system, such as alkyl, trifluoromethyl, esters and nitro groups as well as various halides.

For aliphatic olefins such as 1-octene, lower reaction temperature of 35° C. is needed to obtain higher aldehyde selectivity. 70% aldehyde selectivity at 49% total yield of oxidized products could be obtained. A 5% CuCl$_2$ (with respect to 1-octene) co-oxidant is necessary in this oxidation process. Without CuCl$_2$, a reversal in selectivity occurred to give mainly the Markonikov product, the ketone, with only 33% selectivity (aldehyde:ketone 0.5:1) for aldehyde at 31% combined yield, in 2 h. Alternatively, a higher selectivity of 78% at 37% total yield can be obtained when the reaction is carried out in a nitrogen atmosphere and using anhydrous t-BuOH solvent instead. When 4-methylhexene is used as substrate, high aldehyde selectivity of 90% at 64% total yield could be obtained. Functional groups such as carboxylic acids, esters, dienes and halides are tolerated by this new catalytic system.

What is claimed is:

1. A method for forming an olefin hydration product, the method comprising combining
   a first catalyst comprising platinum or palladium,
   a second catalyst comprising ruthenium, rhodium, iron, or iridium,
   an oxidant,
   an organic reductant,
   an olefin reactant, and
   water
   in a reaction vessel to form a reaction mixture, and allowing the reaction mixture to react for a period of time to form the olefin hydration product, the olefin hydration product comprising an alcohol; wherein,
   the first catalyst is reduced during its reaction with the olefin reactant to generate an oxidized olefin intermediate, the oxidant being capable of re-oxidizing the reduced first catalyst to reform the first catalyst; and
   the second catalyst is inactivated during a reaction with the oxidized olefin intermediate to form the olefin hydration product, the organic reductant being capable of reducing the inactivated second catalyst to reform the second catalyst.

2. The method of claim 1, wherein the olefin reactant is an asymmetric olefin, and wherein the olefin hydration product comprises 50% or more of an anti-Markovnikov hydration product.

3. The method of claim 1, wherein the second catalyst is a hydride of ruthenium, rhodium, iron, or iridium.

4. The method of claim 1, wherein the oxidant comprises copper (II) chloride and an optionally substituted quinone.

5. The method of claim 1, wherein the organic reductant is a secondary alcohol.

6. The method of claim 5, wherein the reaction mixture further comprises a tertiary alcohol or tertiary silanol.

7. The method of claim 2, wherein, when the asymmetric olefin is a terminal olefin, the olefin hydration product comprises a primary alcohol and a secondary alcohol, and wherein the ratio of the primary to secondary alcohols is about 2:1 or greater.

8. The method of claim 1, wherein the allowing the reaction mixture to react comprises catalytically oxidizing an olefin reactant to form the oxidized olefin intermediate having the structure of formula (III)

$$(R^1)(R^2)(H)C—C(=O)(R^3) \quad (III)$$

wherein $R^1$, $R^2$, and $R^3$ are independently H, optionally substituted $C_{1-24}$ alkyl, optionally substituted $C_{5-30}$ aryl, optionally substituted $C_{6-30}$ aralkyl, optionally substituted $C_{1-24}$ alkoxy, optionally substituted aryloxy, optionally substituted $C_{2-24}$ alkylcarbonyl, or optionally substituted $C_{6-20}$ arylcarbonyl, the optional substituents comprising acyl, acyloxy, alkoxy, aryloxy, carboxy, cyano, halo, hydroxy, nitro, $C_{1-6}$ alkyl, —CF$_3$, or a combination or plurality thereof;
   provided that at least one of $R^1$, $R^2$, and $R^3$ is a non-hydrogen substituent, and further provided that, if $R^3$ is not hydrogen, then both $R^1$ and $R^2$ are non-hydrogen.

9. The method of claim 8, wherein the allowing the reaction mixture to react comprises catalytically reducing the intermediate to form an alcohol having the structure of formula (IV)

$$(R^1)(R^2)(H)C—C(H)(OH)(R^3) \quad (IV)$$

wherein $R^1$, $R^2$, and $R^3$ are as defined for formula (III).

10. The method of claim 9, wherein the intermediate is not purified or otherwise isolated prior to the catalytically reducing.

11. A method for forming a product organic alcohol, the method comprising:
(a) contacting an olefin reactant containing an asymmetrically substituted olefin with a first catalyst comprising platinum or palladium in the presence of a tertiary alcohol or tertiary silanol and water to form a carbonyl-containing compound, and reduced first catalyst;
(b) contacting the reduced first catalyst with an oxidant to reform the first catalyst;
(c) contacting the carbonyl-containing compound with a second catalyst comprising ruthenium, rhodium, iron, or iridium to form the product organic alcohol and inactivated second catalyst; and
(d) contacting the inactivated second catalyst with an organic reductant to reform the second catalyst.

12. The method of claim 11, wherein steps (a) through (d) are performed in one reaction vessel.

13. A method for forming an oxidation product, the method comprising combining a catalyst comprising platinum or palladium, an oxidant, a sterically bulky alcohol or silanol, and an olefin reactant to form a reaction mixture in a reaction vessel, and allowing the reaction mixture to react for a period of time to form the oxidation product, wherein the oxidation product comprises an anti-Markovnikov oxidation product and a Markovnikov oxidation product in a ratio of about 2:1 or greater, the oxidation product comprising an aldehyde, ketone, vinyl ether, or mixture thereof.

14. The method of claim 13, wherein the sterically bulky alcohol is a tertiary alcohol or tertiary silanol, the catalyst is capable of catalyzing an oxidation reaction, and the olefin reactant comprises a terminal olefin.

15. The method of claim 1, wherein the olefin reactant is an optionally substituted styrene or vinyl naphthalene, the styrene or vinyl naphthalene optionally substituted with at least one $C_{1-6}$ alkyl, halo, nitro, —$CF_3$, or a combination thereof, the reaction providing a hydration product exhibiting a ratio of primary to secondary alcohols greater than 20:1.

16. The method of claim 1, wherein the oxidant comprises copper or iron chloride, a chromium oxide, manganese dioxide, silver oxide, hydrogen peroxide, benzoyl peroxide, a quinone or substituted quinone, oxygen, or ozone.

17. The method of claim 4, wherein the optionally substituted quinone is benzoquinone.

18. The method of claim 5, wherein the secondary alcohol is isopropanol.

19. The method of claim 6, wherein the olefin hydration product comprises a primary alcohol and a secondary alcohol, and wherein the ratio of the primary to secondary alcohols is about 2:1 or greater.

20. The method of claim 11, wherein the organic reductant is a secondary alcohol.

21. The method of claim 13, wherein the sterically bulky alcohol or silanol is tert-butanol, adamantanol, trimethylsilanol, or a combination thereof.

22. The method of claim 13, wherein the reaction mixture is anhydrous, and the oxidation product is a vinyl ether.

23. The method of claim 13, wherein the reaction mixture further comprises water, and the oxidation product comprising an aldehyde, ketone, or mixture thereof.

24. The method of claim 13, wherein the oxidant comprises copper (II) chloride and an optionally substituted quinone.

25. The method of claim 1, wherein the first catalyst comprises $PdCl_2(MeCN)_2$.

26. The method of claim 1, wherein the second catalyst comprises 1-hydroxytetraphenylcyclopentadienyl-(tetraphenyl-2,4-cyclopentadien-1-one)-µ-hydrotetracarbonyldiruthenium(II).

27. The method of claim 1, wherein:
the first catalyst comprises $PdCl_2(MeCN)_2$;
the second catalyst comprises 1-hydroxytetraphenylcyclopentadienyl-(tetraphenyl-2,4-cyclopentadien-1-one)-µ-hydrotetracarbonyldiruthenium(II),
the oxidant comprises copper (II) chloride and benzoquinone;
the organic reductant comprises isopropanol; and
the reaction mixture further comprises tert-butanol.

28. The method of claim 11, wherein the first catalyst comprises $PdCl_2(MeCN)_2$.

29. The method of claim 11, wherein the oxidant comprises copper (II) chloride and an optionally substituted quinone.

30. The method of claim 11, wherein the second catalyst comprises 1-hydroxytetraphenylcyclopentadienyl-(tetraphenyl-2,4-cyclopentadien-1-one)-µ-hydrotetracarbonyldiruthenium(II).

31. The method of claim 11, wherein the asymmetrically substituted olefin is a terminal olefin.

32. The method of claim 11, wherein the asymmetrically substituted olefin is an optionally substituted styrene or vinyl naphthalene, the styrene or vinyl naphthalene optionally substituted with at least one $C_{1-6}$ alkyl, halo, nitro, -$CF_3$, or a combination thereof.

33. The method of claim 11, wherein:
the first catalyst comprises $PdCl_2(MeCN)_2$;
the second catalyst comprises 1-hydroxytetraphenylcyclopentadienyl-(tetraphenyl-2,4-cyclopentadien-1-one)-µ-hydrotetracarbonyldiruthenium(II),
the oxidant comprises copper (II) chloride and benzoquinone;
the organic reductant comprises isopropanol; and
the tertiary alcohol or tertiary silanol comprises tert-butanol.

34. The method of claim 13, wherein the catalyst comprises $PdCl_2(MeCN)_2$.

35. The method of claim 13, wherein the asymmetrically substituted olefin is a terminal olefin.

36. The method of claim 13, wherein the asymmetrically substituted olefin is an optionally substituted styrene or vinyl naphthalene, the styrene or vinyl naphthalene optionally substituted with at least one $C_{1-6}$ alkyl, halo, nitro, -$CF_3$, or a combination thereof 37. The method of claim 13, wherein
the catalyst comprises $PdCl_2(MeCN)_2$,
the oxidant comprises copper (II) chloride and benzoquinone; and
the sterically bulky alcohol or silanol comprises tert-butanol.

* * * * *